US009328962B2

(12) United States Patent
Lee et al.

(10) Patent No.: US 9,328,962 B2
(45) Date of Patent: May 3, 2016

(54) APPARATUS AND METHODS TO OPERATE A MICROREACTOR

(71) Applicant: Pharyx, Inc., Woburn, MA (US)

(72) Inventors: Harry Lee, Malden, MA (US); Kevin Shao-Kwan Lee, Cambridge, MA (US)

(73) Assignee: Pharyx, Inc., Woburn, MA (US)

( * ) Notice: Subject to any disclaimer, the term of this patent is extended or adjusted under 35 U.S.C. 154(b) by 497 days.

(21) Appl. No.: 13/750,982

(22) Filed: Jan. 25, 2013

(65) Prior Publication Data

US 2013/0196276 A1   Aug. 1, 2013

Related U.S. Application Data

(60) Provisional application No. 61/590,861, filed on Jan. 26, 2012.

(51) Int. Cl.
| F27D 7/00 | (2006.01) |
| C12M 3/06 | (2006.01) |
| C12M 1/00 | (2006.01) |
| C12M 1/02 | (2006.01) |
| B01J 19/00 | (2006.01) |
| B01L 3/00 | (2006.01) |
| B01L 7/00 | (2006.01) |

(52) U.S. Cl.
CPC .............. *F27D 7/00* (2013.01); *B01J 19/0093* (2013.01); *B01L 3/502715* (2013.01); *B01L 7/00* (2013.01); *C12M 23/16* (2013.01); *C12M 29/14* (2013.01); *C12M 41/22* (2013.01); *B01J 2219/0095* (2013.01); *B01J 2219/0097* (2013.01); *B01J 2219/00813* (2013.01); *B01J 2219/00817* (2013.01); *B01J 2219/00873* (2013.01); *B01J 2219/00961* (2013.01); *B01L 2200/027* (2013.01); *B01L 2300/043* (2013.01); *B01L 2300/0816* (2013.01); *B01L 2300/1805* (2013.01); *B01L 2400/0487* (2013.01); *Y10T 29/49826* (2015.01); *Y10T 29/53* (2015.01)

(58) Field of Classification Search
CPC .......................... B01L 9/527; B01L 2200/027
See application file for complete search history.

(56) References Cited

U.S. PATENT DOCUMENTS

| 3,865,411 | A | 2/1975 | Rowe | |
| 5,458,008 | A | 10/1995 | Rassatt | |
| 6,632,404 | B1 * | 10/2003 | Freitag et al. | 506/33 |
| 2003/0096081 | A1 * | 5/2003 | Lavallee et al. | 428/138 |
| 2004/0202581 | A1 * | 10/2004 | Berndt | 422/100 |
| 2005/0170493 | A1 * | 8/2005 | Patno et al. | 435/287.2 |
| 2006/0121624 | A1 * | 6/2006 | Huang et al. | 436/180 |
| 2006/0163069 | A1 * | 7/2006 | Prak et al. | 204/601 |
| 2007/0080063 | A1 * | 4/2007 | Kennedy et al. | 204/451 |
| 2008/0241909 | A1 | 10/2008 | Jung et al. | |
| 2011/0053806 | A1 | 3/2011 | Amin | |
| 2011/0076759 | A1 | 3/2011 | Reif | |

* cited by examiner

*Primary Examiner* — Jill Warden
*Assistant Examiner* — Matthew Krcha
(74) *Attorney, Agent, or Firm* — May Ming Wu

(57) ABSTRACT

The present invention provides apparatus and methods to operate microreactor devices through the controlled delivery of pressurized fluids. A heated reservoir, a heated manifold, and a heater for the microreactor device provides for the delivery of a pressurized gas while minimizing evaporation and condensation; and a fluid interface and pressure interlock provides for the delivery of aseptic fluids while minimizing contamination and fluid loss.

18 Claims, 15 Drawing Sheets

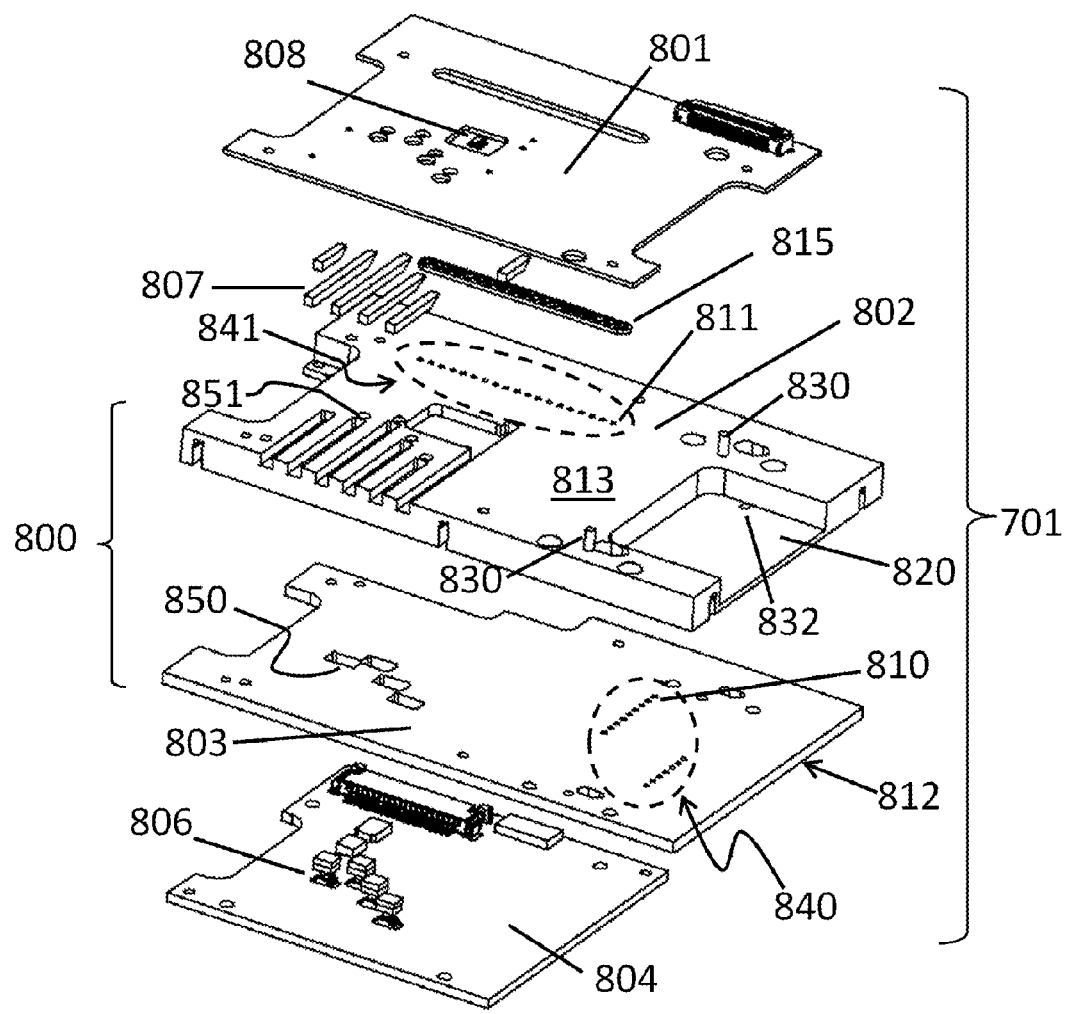

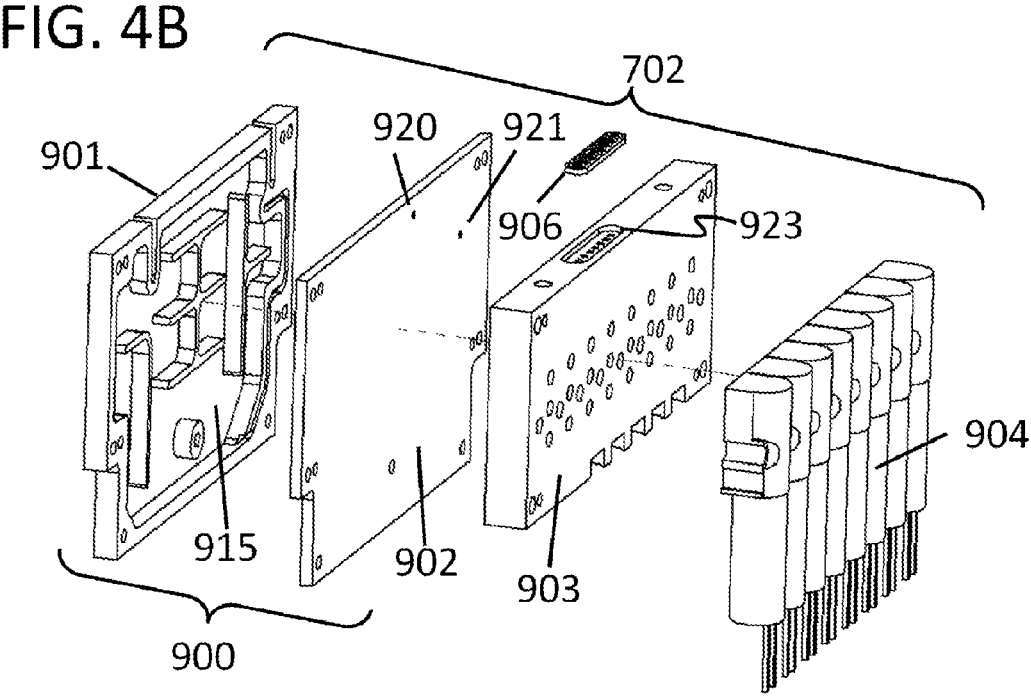
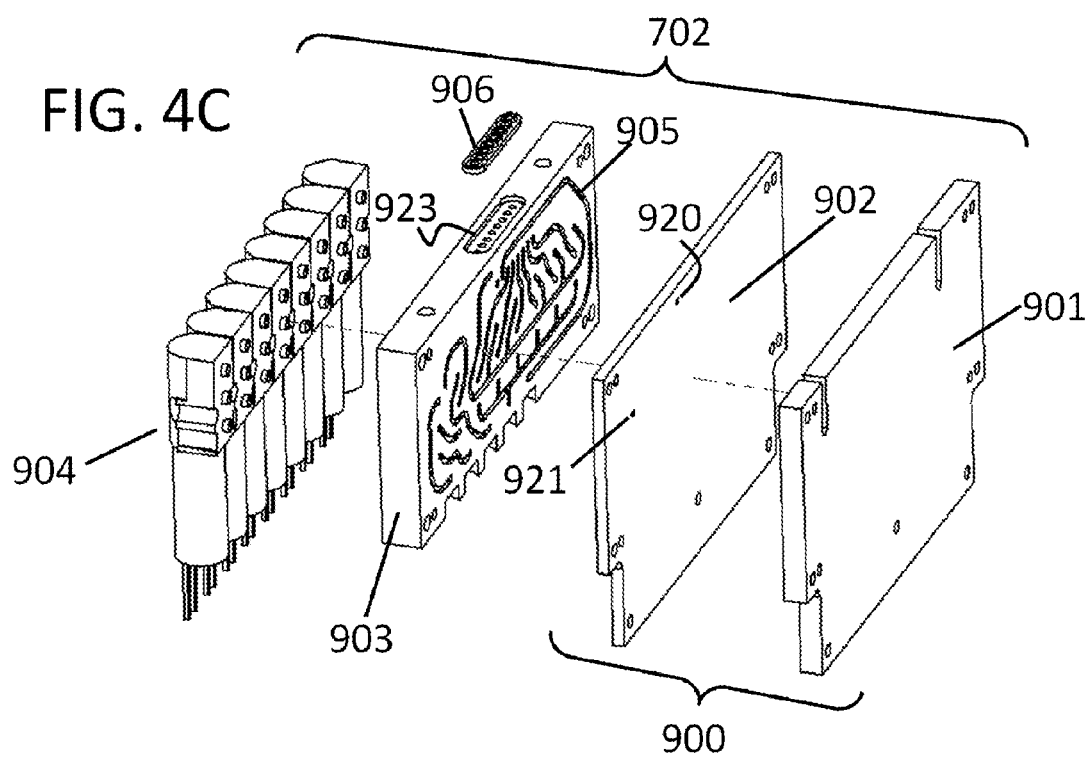

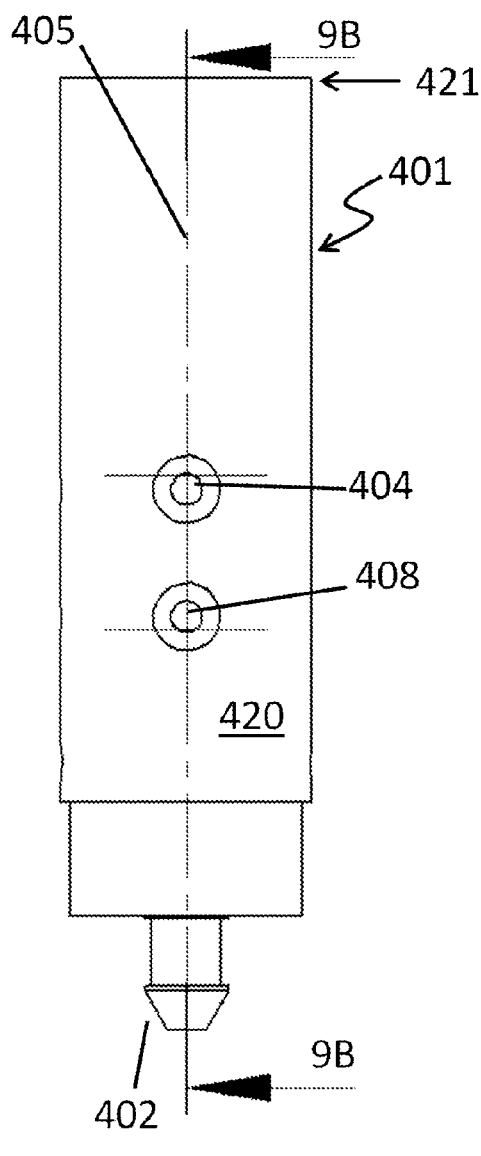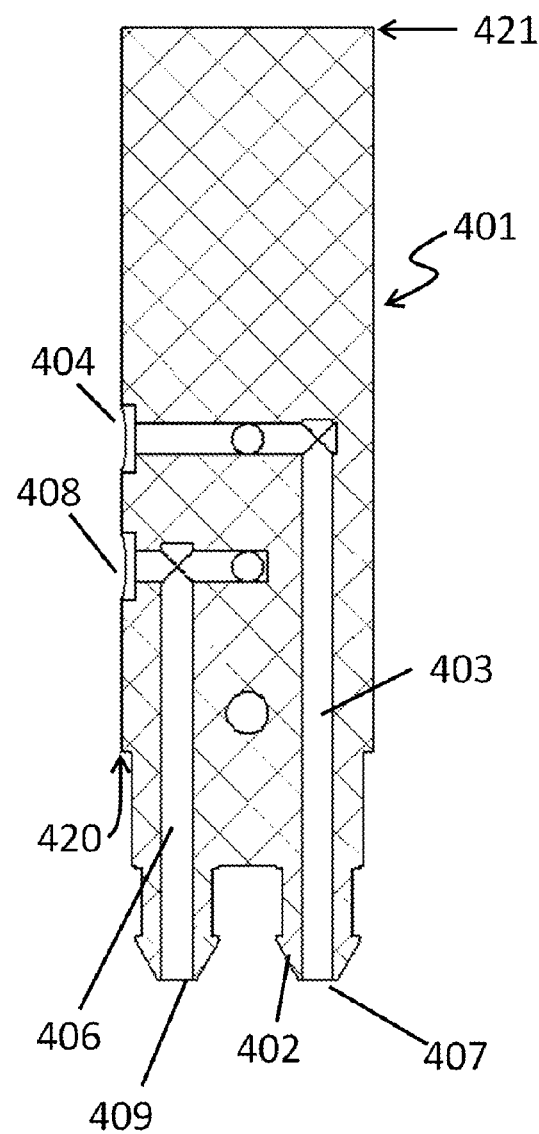
FIG. 9A
FIG. 9B

APPARATUS AND METHODS TO OPERATE A MICROREACTOR

RELATED APPLICATIONS

This application claims priority from U.S. Provisional Application No. 61/590,861, entitled "Systems, apparatus, and methods to operate small bioreactors" filed Jan. 26, 2012, the content of which is hereby incorporated by reference in its entirety.

STATEMENT REGARDING FEDERALLY SPONSORED RESEARCH OR DEVELOPMENT

This work was funded under federal grant number DE-FG02-08ER85207.

TECHNICAL FIELD

The field of the invention relates to apparatus and methods to interface and operate small scale microreactor devices.

BACKGROUND OF THE INVENTION

All referenced patents and applications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

Small scale bioreactors are intended to reduce the effort required to perform complicated fermentation and cell culture experiments, such as continuous cultures, and to provide the possibility of conducting these experiments in parallel. Continuous culture experiments, described for example in US2011/0053806A1, require the aseptic introduction of large volumes of fluid to the microfluidic device, typically many times the internal device volume. This requires an aseptic interconnection between at least one large volume aseptic reservoir and the aseptic microfluidic device. For parallel experiments, performing many of these aseptic connections efficiently is important. Conventional means to perform aseptic connections include the use of septa that block openings to channels in the microfluidic device, for example as in US2008/0241909A1 and puncturing the septa with a sterile needle connected to a source of sterile fluid, or making manual tubing connections between the fluid sources and the microfluidic device in a sterile environment. These methods require manual dexterity and are inconvenient when setting up many experiments.

There is also the requirement to supply a driving force to introduce the fluid into the device. This is typically done by supplying the fluid at a higher pressure than the fluid pressure in the device to generate a pressure driven flow. Under these conditions, with the fluid source at a pressure higher than the device, there is a risk of unintentional introduction of fluid to the area around the device should it be disconnected before equalizing the fluid pressure to atmospheric pressure. The unintentionally released fluid could damage sensitive equipment or contaminate clean surfaces.

An additional consideration for small scale bioreactors is loss of fluid due to evaporation. This is due to the large surface area to volume ratio of typical microfluidic devices. Minimizing fluid loss due to evaporation is important in order to minimize changes in the concentration of nutrients. Minimization of evaporation is particularly challenging because of the relatively high rate of gas exchange required to provide mixing and oxygenation to growing organisms. One approach to minimizing evaporation is to ensure the relative humidity of the gas that is exchanged with the bioreactor is near 100%. However, maintaining a high relative humidity of the gas increases the risk of condensation. Condensation of water has the negative effects of clogging channels designed for gas flow with liquid, and also interfering with optical or electrical measurements. To reduce or prevent condensation, any surfaces in contact with the humidified gas are set to temperatures higher than the condensation temperature of the humidified gas or the gas is dehumidified before reaching the surfaces of interest as in US5458008. However, since it is necessary to provide humidified gas to the devices performing liquid and gas reactions, dehumidifying the gas to prevent condensation before reaching the device is detrimental to system operation since it will not prevent fluid loss. Yet another method employed by US 2011/0076759 A1 is to implement a condenser at the output of the device to prevent evaporated liquid from leaving the device. While this method works in larger systems, smaller systems typically cannot afford to have cold regions close to temperature controlled or heated regions and systems relying on membranes for gas transfer have no method of returning condensed liquid to the device for reuse.

Thus, there is a need for an apparatus and methods to operate microfluidic bioreactors that provides convenient aseptic connections between microfluidic devices and large volume fluid reservoirs; mechanisms to reduce the chance of unintentional introduction of fluid around the device; and minimization of evaporation while at the same time avoiding condensation. In addition, such apparatus and methods should be efficient enough to use for many microfluidic bioreactors operated in parallel.

REFERENCED DOCUMENTS

All referenced documents are hereby incorporated in their entirety.
US2011/0053806A1
US2008/0241909A1
U.S. Pat. No. 5,458,008
2011/0076759 A1
U.S. Pat. No. 3,865,411

SUMMARY OF INVENTION

The present invention provides, apparatus and methods to interface to and operate a microreactor device through the controlled exchange of pressurized fluids with sources external to the microreactor device.

In preferred embodiments, a gas from a pressure source is delivered to a reservoir that is heated by thermal contact with a temperature controlled base plate. It is contemplated that water may be introduced to the reservoir to humidify the gas. The temperature controlled base plate comprises conduits with an openings on either side of the base plate to allow gas to remain heated and to pass from the reservoir to the microreactor device through solenoid switches which control the gas flow through each conduit. The temperature of the microreactor device is controlled through heating by thermal contact with the base plate on the bottom and thermal contact with a top heater. It is contemplated that maintaining the top heater temperature above the base plate temperature will prevent condensation. While in a preferred embodiment, conduits in the base plate have an opening on either side of the base plate, it is also contemplated that both openings are on the same side.

Another aspect of preferred embodiments is the mechanical mounting of the top heater by a hinged lid with protruding spring pins. The top heater is pulled against the spring pins by extension springs, allowing the heater to move laterally for alignment with the microreactor device. When the top lid is closed the spring pins push the heater against the microreactor device. Yet another aspect of preferred embodiments is a gasket and clamp to form a seal between the microreactor device and conduit in the base plate.

Another aspect of preferred embodiments is the interrogation of optical sensors in the microreactor device using a light emitting diode to excite the sensor, a waveguide to collect sensor emission and a photodiode to convert the optical signal to an electrical signal for processing.

It is further contemplated that in addition to delivering a gas to the microreactor, liquids from external sources may be delivered as well, including the delivery of liquids aseptically, preferably from sterilizable containers. Preferred embodiments include a fluid interface to translate fluid paths arriving from conduits of arbitrary size and form factor to the fluid paths of the microreactor device. It is contemplated that the fluid interface has conduits with openings on a substantially planar surface that correspond to openings on the microreactor device. A cavity in the base plate allows mounting of the fluid interface such that a gasket with corresponding openings can form a seal between the fluid interface and the microreactor device when the microreactor device is clamped onto the base plate.

In yet another aspect of preferred embodiments, a pressure interlock combines the mechanical action of preventing the clamp that seals the microreactor device to the fluid interface gasket from being removed with the act of pressurizing the fluid to be delivered through the fluid interface to the microreactor device. In a preferred embodiment, the pressure interlock comprises a prism having two conduits within, each conduit having an opening on the radial surface of the prism, and another opening on an axial surface of the prism. A preferred embodiment further comprises a cavity in a structural panel with openings having similar cross sectional area as the prism on each opposing side of the panel. A seal at each opening enables the formation of an enclosed volume when the prism is inserted through both openings. The axial position of the radial conduit openings is chosen such that when the structure panel is in a fixed position with respect to the clamped position of the clamp, and the prism, when inserted through the openings of the structure panel prevent the removal of the clamp, the two openings are in fluid communication within the cavity, and when the prism is moved so as not to block to removal of the clamp, one of the openings is outside of the cavity.

Another aspect of preferred embodiments provides methods to operate a microreactor device comprising the steps of controlling the temperature of the base plate to a first temperature range, controlling the temperature of the top heater to a second temperature range, and opening and closing a solenoid switch. Additional steps are contemplated including controlling the temperature of the reservoir to a third temperature range, introducing a fluid into the reservoir, constraining the first temperature range to be less than or equal to the second temperature range, and constraining the third temperature range to be less than the first temperature range.

Yet another aspect of preferred embodiments of the invention provides methods to exchange fluid with the microreactor device comprising the steps of inserting the fluid interface into the cavity of the base plate, aligning openings of the microreactor device to openings in gaskets, clamping the microreactor to the gaskets. Additional steps are contemplated including applying sterilizable tape to the fluid interface and microreactor device, sterilizing fluid containers, the fluid interface, and fluid conduits, introducing sterilized fluids to the containers, aligning the openings of the microreactor to openings in the gaskets, simultaneously removing the sterilizable tapes covering the fluid interface and microreactor, clamping the microreactor to the gaskets, and configuring a prism in a position to pressurize the fluid and prevent the clamp from being removed.

Embodiments of these and other aspects of the invention are described in more detail in the description that follows.

BRIEF DESCRIPTION OF THE DRAWINGS

The embodiments of the present invention will now be described by reference to the following figures, in which identical reference numerals in different figures indicate identical elements and in which:

FIG. 3A shows an exploded view of a heated base plate manifold assembly.

FIG. 4B shows an exploded view of the humidifier manifold and solenoid assembly from one angle.

FIG. 4C shows and exploded view of the humidifier manifold and solenoid assembly from a second angle.

FIG. 9A shows a top view of a pressure connector.

FIG. 9B shows a cross-section view of a pressure connector.

Figure 1:
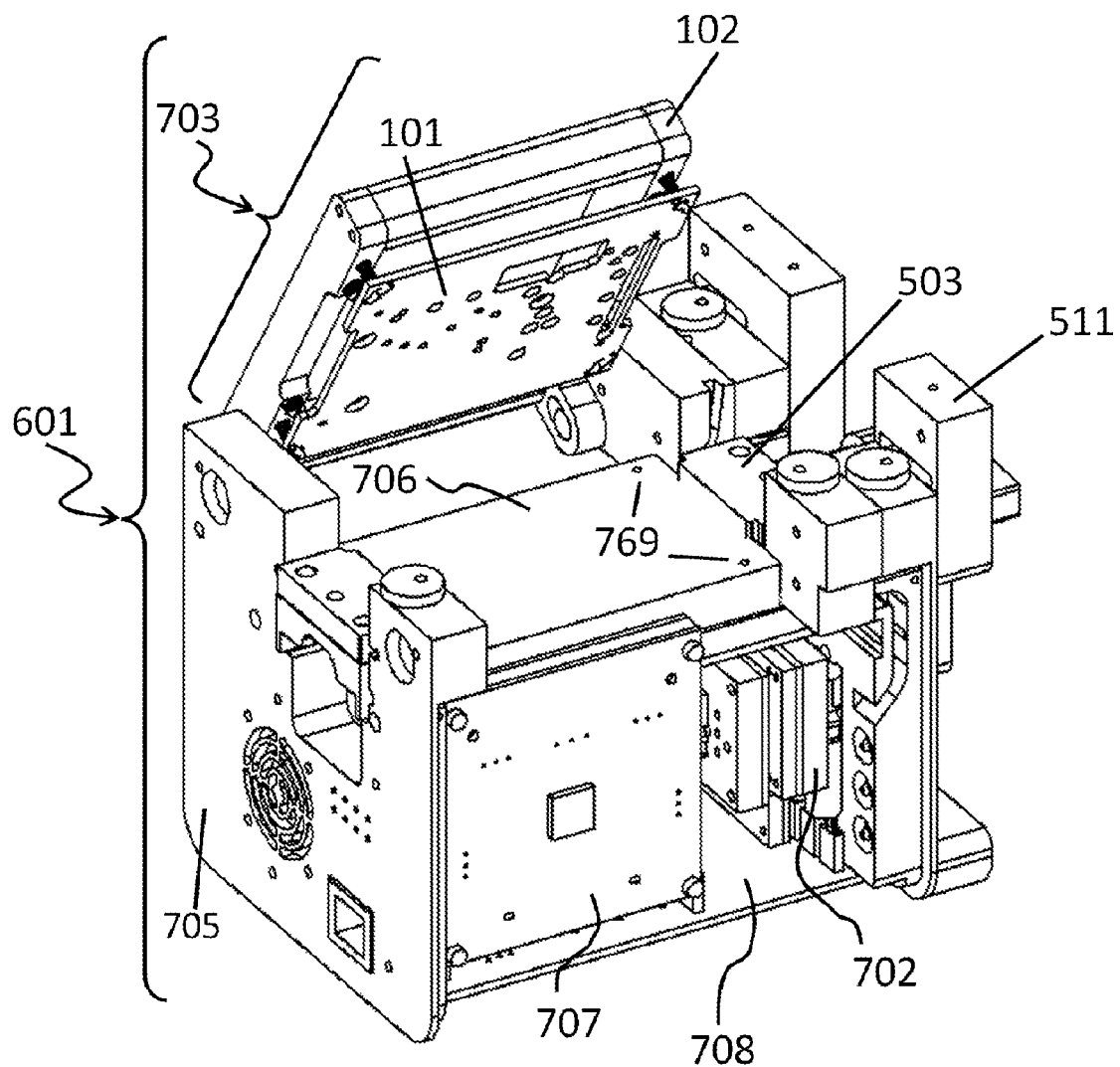
FIG. 1 shows a microreactor controller.

LEGEND FOR DRAWING REFERENCE LABELS 101 top heater
102 hinged lid frame 103 hinge pin hole
104 mechanical support (dowel pin)
105 Extension spring
106 alignment holes
107 spring pin
108 mechanical support for heater (dowel pin)
200 fluid interface
201 fluid interface body
202 protruding rings
203 hose barbs
204 openings inside a protruding ring
205 fluid interface gasket
206 conduit in fluid communication with the fluid interface body
207 direct tube through fluid interface
208 flare
210 internal conduit in fluid interface
212 first opening of fluid interface conduit
213 second opening of fluid interface conduit
214 first side of the body
215 second side of the body
217 opening in gasket
220 alignment posts
230 opening for direct tube in fluid interface body
231 opening in gasket for direct tube
305 surface of device that contacts fluid gasket
306 protruding rings of microreactor (smaller)
308 protruding rings on the microreactor
401 pressure connector
402 barb
403 first conduit within pressure connector
404 first opening of first conduit
405 section line
406 second conduit within pressure connector
407 second opening of first conduit
408 first opening of second conduit
409 second opening of second conduit
420 radial face of pressure connector
421 axial face of pressure connector
501 section line
503 clamp
504 clamp base
506 springs
507 pivot point
508 housing
511 structural panel
512 cavity
513 seals
515 locking mechanism
601 microreactor controller
701 heated base plate manifold assembly
702 humidifier manifold and solenoid assembly
703 lid assembly
704 pressure interlock and fluid interface assembly
705 connector panel group
706 microreactor device
707 photodiode board assembly
708 power and solenoid driver board
709 digital control module
710 valve-side solenoid manifold assembly
761 microreactor first side
762 microreactor second side
765 first opening
766 second opening
767 first group of openings
768 second group of openings
769 alignment holes
770 conduit within microreactor for air
800 heated base plate manifold
801 middle heater
802 base plate top
803 base plate bottom
804 bottom heater
805 manifold channels
806 LED
807 waveguide
808 temperature sensors
810 first opening
811 second opening
812 first surface
813 second surface
815 first gasket
820 cavity in base plate
830 cylindrical posts part of aligner for microreactor device
840 base plate first group of openings
841 base plate second group of openings
850 openings in base plate bottom
851 openings in base plate top
900 humidifier reservoir
901 reservoir layer
902 reservoir capping layer
903 solenoid manifold
904 solenoids
905 solenoid manifold channels
906 solenoid manifold gasket
910 first pressure source
912 second pressure source
915 cavity of humidifier reservoir
920 first opening in reservoir capping layer
921 second opening in reservoir capping layer
923 openings at top edge of solenoid manifold
1001 fluid bottle
1002 section line
1003 bottle cap
1004 insert for tubing connections
1005 inside barbs
1006 tubing
1007 ring
1008 o-ring
1009 outside barbs
1012 outlet of bottle
1022 inlet to bottle

DETAILED DESCRIPTION OF THE INVENTION

Detailed Description of the Drawing

The drawing refers to preferred embodiments of the invention and the particular components, materials, and dimensions, as well as other details are to be interpreted to apply broadly in the art and should not be construed to unduly restrict or limit the invention in any way.

Referring now to a preferred embodiment in more detail, FIG. 1 shows an isometric view of a microreactor controller 601 used to operate a microreactor device 706. The microreactor controller comprises: a lid assembly 703 comprising a top heater 101, a hinged lid 102, a photodiode board assembly 707, a humidifier reservoir and solenoid assembly 702, a clamp 503, a power and solenoid driver board 708, and a structure panel 511. Also shown are two alignment holes 769 of the microreactor device 706. The photodiode board assembly 707 comprises photodiodes and amplifier electronics coupled to an analog to digital conversion board. The power and solenoid driver board 708 comprises DC-DC converters and solenoid driver amplifiers.

Figure 2A:
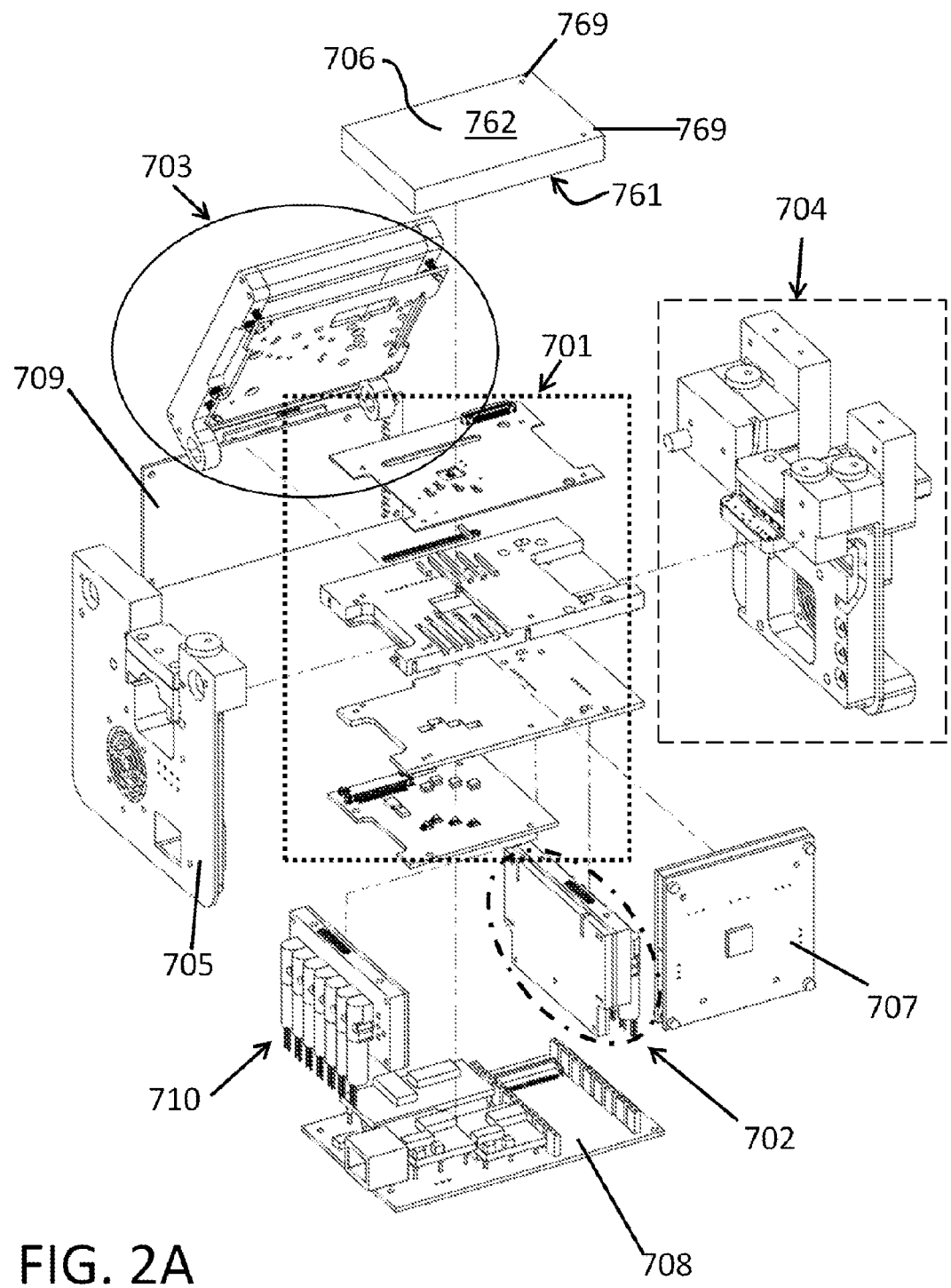
FIG. 2A shows an exploded view of the microreactor controller.

FIG. 2A shows an exploded view of the microreactor controller 601. For the purposes of a more detailed description, the microreactor controller comprises four main groups, a heated base plate manifold assembly 701, a humidifier manifold and solenoid assembly 702, a lid assembly 703, and a pressure interlock and fluid interface assembly 704, as well as the additional components of a photodiode board assembly 707, a power and solenoid driver board 708, a connector panel 705, a digital control module 709 comprising a field programmable gate array, and a valve-side solenoid manifold assembly 710. Also shown is an outline of a microreactor device 706, having a first side 761, a second side 762, and two alignment holes 769.

Figure 2B:
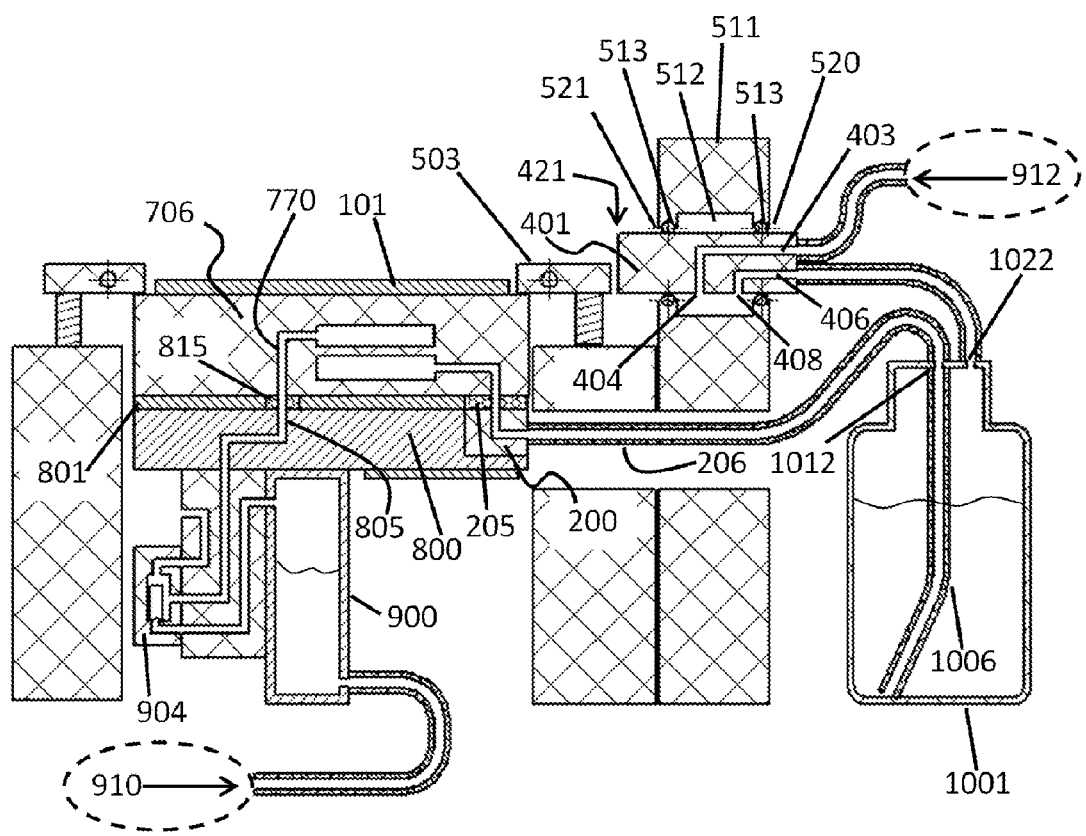
FIG. 2B shows a schematic side view of a microreactor controller.

FIG. 2B shows a schematic view of a microreactor controller, highlighting the aspects related to delivery of fluids to a microreactor device 706. To deliver humidified gas to the microreactor device 706 to minimize evaporation, while at the same time minimizing condensation, the temperature of the humidified gas must not decrease below the dew point. It is therefore preferred to heat all of the surfaces between the generation of humid gas through the delivery of the humid gas to the microreactor device. This can be accomplished by coupling a humidifier reservoir 900 comprising a thermally conductive material to a heated base plate manifold 800. Pressurized humid gas is generated by coupling a first pressure source 910 to the humidifier reservoir 900, which comprises a volume of water. The pressurized humidified gas can then be selectively introduced to a conduit 805 within the heated base plate manifold that is in fluid communication with a conduit 770 within the microreactor device 706 by actuating a solenoid switch 904. To minimize condensation it is preferred to heat the microreactor device 706 uniformly from both the top and bottom. Heat from the bottom comes from a middle heater 801 and thermal contact with the heated base plate manifold 800. Heat from the top comes from a top heater 101. To interface a microreactor 706 with a liquid, preferably aseptic liquids, it is preferred to use a removable fluid container 1001 and fluid interface 200 so that they may be separately sterilized from the rest of the microreactor controller. The fluid interface 200 translates the form factor of the fluid conduits 206, into a format that is compatible with the microreactor device. An example is the translation between ⅛ inch diameter tubing to an array of 0.036 inch openings. By utilizing aligners, where mating geometrical features constrain the position of the microreactor or other components with a reference component, such as the heated base plate manifold 800, microreactor devices requiring many pneumatic signals and many fluid feeds can be conveniently interfaced where a seal between the openings in the heated base plate manifold 800 and fluid interface 200 are accomplished with gaskets 815 and 205 and a clamp 503 or multiple clamps to press the microreactor device 706 onto the gaskets 815 and 205, forming a seal.

Because fluid delivery to the microreactor device depends on pressure driven flow, liquids must be supplied under pressure. This introduces a risk that if the user accidentally removes the clamp 503, liquid will flow out of the fluid interface and flow to undesirable locations. To prevent this problem, it is preferred to use a pressure interlock that prevents removal of the clamp when the fluid is pressurized. This can be accomplished with a structural panel 511 comprising a cavity 512 with openings 520 and 521 on either side of the structural panel 511. Seals at each opening 520 and 521 allow a sealed enclosed volume to be formed when a pressure connector 401 in the shape of a prism is inserted into the openings 520 and 521. The pressure connector has two conduits 403 and 406 with corresponding openings 404 and 408 on the radial surface of the pressure connector 401. When the pressure connector 401 is inserted into the cavity 512 such that the two openings 404 and 408 are between the seals 513, conduits 403 and 406 are in fluid communication within the cavity and pressure from a second pressure source 912 is transmitted from conduit 403 to conduit 406 and subsequently the bottle 1001. In this configuration the pressure connector 401 blocks the clamp 503 from being removed. When the pressure connector is moved so that the opening 404 is between the seals and opening 406 is outside of the seals, the bottle 1001 is vented, the pressure source 912 is blocked, and the clamp 503 can be removed.

Figure 3B:
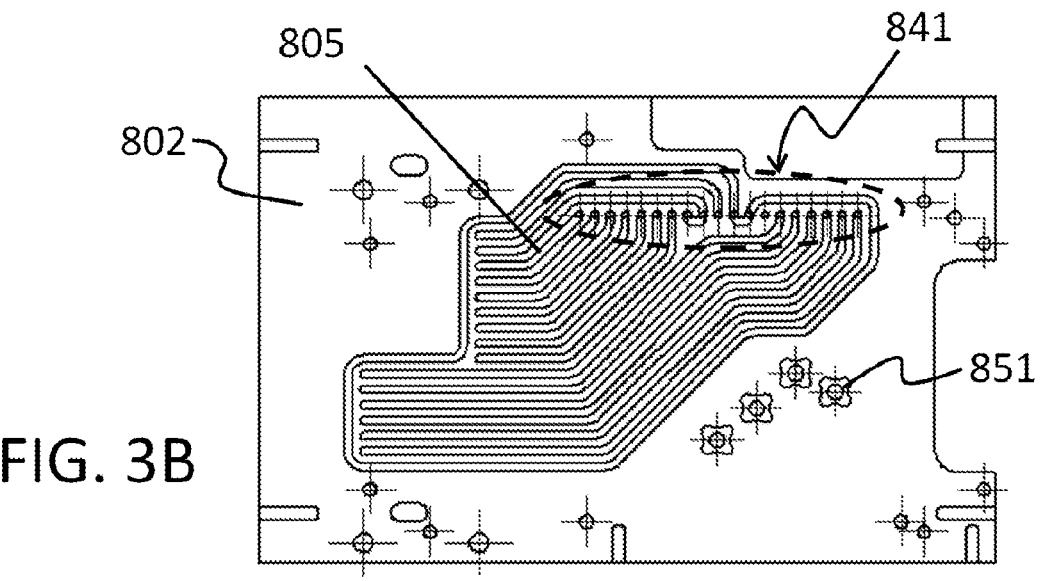
FIG. 3B shows a bottom view of the top layer of the heated base plate manifold.

In more detail FIG. 3A, shows the heated base plate manifold assembly 701 comprising: a middle heater 801; a two layer heated base plate manifold 800 comprising a base plate top 802, and a base plate bottom 803; and a bottom heater 804. A first group of holes 840 in the base plate bottom 803 has a position that corresponds to a first set of endpoints of channels 805 on the bottom of base plate top 802 as shown in FIG. 3B. The second set of endpoints of channels 805 coincide with a second group of holes 841, shown in both FIG. 3A and FIG. 3B. When the base plate top 802 and base plate bottom 803 are bonded together to form a heated base plate manifold 800 using means known in the art, such as using an adhesive film, such as a pressure sensitive silicone adhesive, or other adhesive, the channels 805 and first hole group 840 and second hole group 841 form conduits inside the heated base plate manifold. Middle heater 801 and bottom heater 804 located mounted in thermal communication with, respectively, the base plate top 802 and base plate bottom 803 provide the capability to raise the temperature of the heated base plate manifold 800. It should be clear to one of ordinary skill in the art that temperature control is enabled by measuring the temperature of the heated base plate manifold 800 and adjusting the heating power delivered by the heaters. Cooling the heated base plate manifold 800 can be accomplished using a fan to increase convective heat transfer from the heated base plate manifold 800.

In even more detail in FIG. 3A, middle heater 801 and bottom heater 804 can be made of materials used to make circuit boards such as but not limited to copper, aluminum, fiberglass, epoxy, or gold. Other types of heaters are also possible, such as water jacket heaters or chemical heaters. The heaters in a preferred embodiment can be between 6 square inches and 12 square inches in area, or between 1 and 50 square inches in area and between 0.01 and 0.0625 inches thick or between 0.01 and 0.2 inches thick. Other components for sensing or control, such as waveguides 807, light emitting diodes 806, or temperature sensors 808 may be incorporated as well. In particular it is preferred to mount light emitting diodes 806 on the bottom heater 804 so the light is projected upwards through openings 850 in the base plate bottom 803 and openings 851 in the base plate top 802 to excite optical sensors inside the microreactor devices. Optical emission from the optical sensors can then be collected by the waveguides and transmitted to the photodiodes on the photodiode board assembly 707.

The base plate top 802 and base plate bottom 803 can be made of thermally conductive or thermally capacitive materials such as but not limited to aluminum, copper, iron, or steel to improve temperature uniformity. If temperature uniformity is not important or not an issue due to factors such as thickness or degree of insulation, less thermally conductive or thermally capacitive materials can also be used such as but not limited to polycarbonate, acrylic, polypropylene, peek, or nylon. The base plate top 802 and base plate bottom 803 can be between 6 square inches and 15 square inches in area, or between 1 square inch and 50 square inches in area and between 0.02 and 0.2 inches thick or between 0.01 and 1 inch thick. Channels 805 on the bottom side of the manifold layer 802, can be 0.02 inches wide or between 0.001 and 0.2 inches wide and 0.01 inches deep or between 0.001 and 0.15 inches deep.

Figure 4A:
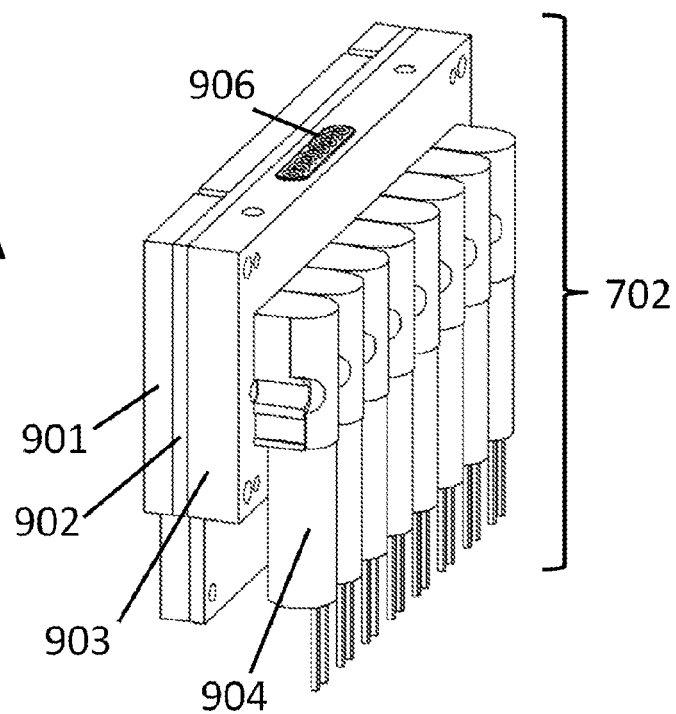
FIG. 4A shows a humidifier manifold and solenoid assembly.

FIG. 4A shows the humidifier manifold and solenoid assembly 702. The exploded view in FIG. 4B shows a humidifier reservoir 900 comprising a reservoir layer 901 and a reservoir capping layer 902, a solenoid manifold 903, and solenoids 904. FIG. 4C shows an exploded view of the humidifier manifold and solenoid assembly 702 from a reverse angle to show the locations of solenoid manifold channels 905 in the solenoid manifold 903.

In more detail, bonding the reservoir layer 901 and reservoir capping layer 902 together using means known in the art such as adhesive bonding with an adhesive film, such as a pressure sensitive silicone adhesive film, or other adhesive forms a humidifier reservoir 900, with a cavity 915 that can be accessed externally through two openings 920 and 921 in the reservoir capping layer 902. Conduits are formed in the solenoid manifold 903 when it is bonded, using means known in the art, to the reservoir capping layer 902. The conduits connect the openings in the reservoir capping layer, and therefore the cavity 915 in the humidifier reservoir 900, with ports of a solenoid switch. In general, the solenoid manifold channels 905 are configured to deliver the appropriate pressure, switched by the solenoids 904 to the openings 923 at the top edge of the solenoid manifold 903. Typically switching is between a supplied pressure and atmospheric pressure. The humidifier manifold and solenoid assembly 702 interfaces with the heated base plate manifold assembly 701 with a solenoid manifold gasket 906. Preferably, the openings 923 at the top edge of the solenoid manifold are aligned with the openings 840 in the heated base plate manifold 800. While a gasket is used in a preferred embodiment, other connection methods can be used such as but not limited to tubes, adhesives, or direct welding.

In more detail in FIG. 4B and FIG. 4C, the reservoir layer 901, and reservoir capping layer 902, and manifold layer 903 can be made of a thermally conductive or thermally capacitive material such as but not limited to aluminum, copper, iron, or steel to improve temperature uniformity. If temperature uniformity is not important or not an issue due to factors such as thickness or degree of insulation, less thermally conductive or thermally capacitive materials can also be used such as but not limited to polycarbonate, acrylic, polypropylene, peek, or nylon. Solenoids 904 can be purchased from a variety of vendors known to those of ordinary skill in the art. The reservoir layer 901, reservoir capping layer 902, and solenoid manifold 903 can be 5 inches square in area or between 0.5 and 20 inches square in area and between 0.02 and 1 inch thick. The gasket 906 can be made of a compressible material such as but not limited to silicone, butyl rubber, EPDM, or viton. The gasket 906 can be between 0.04 and 0.5 inch wide and between 0.1 and 3 inches long.

Figure 5:
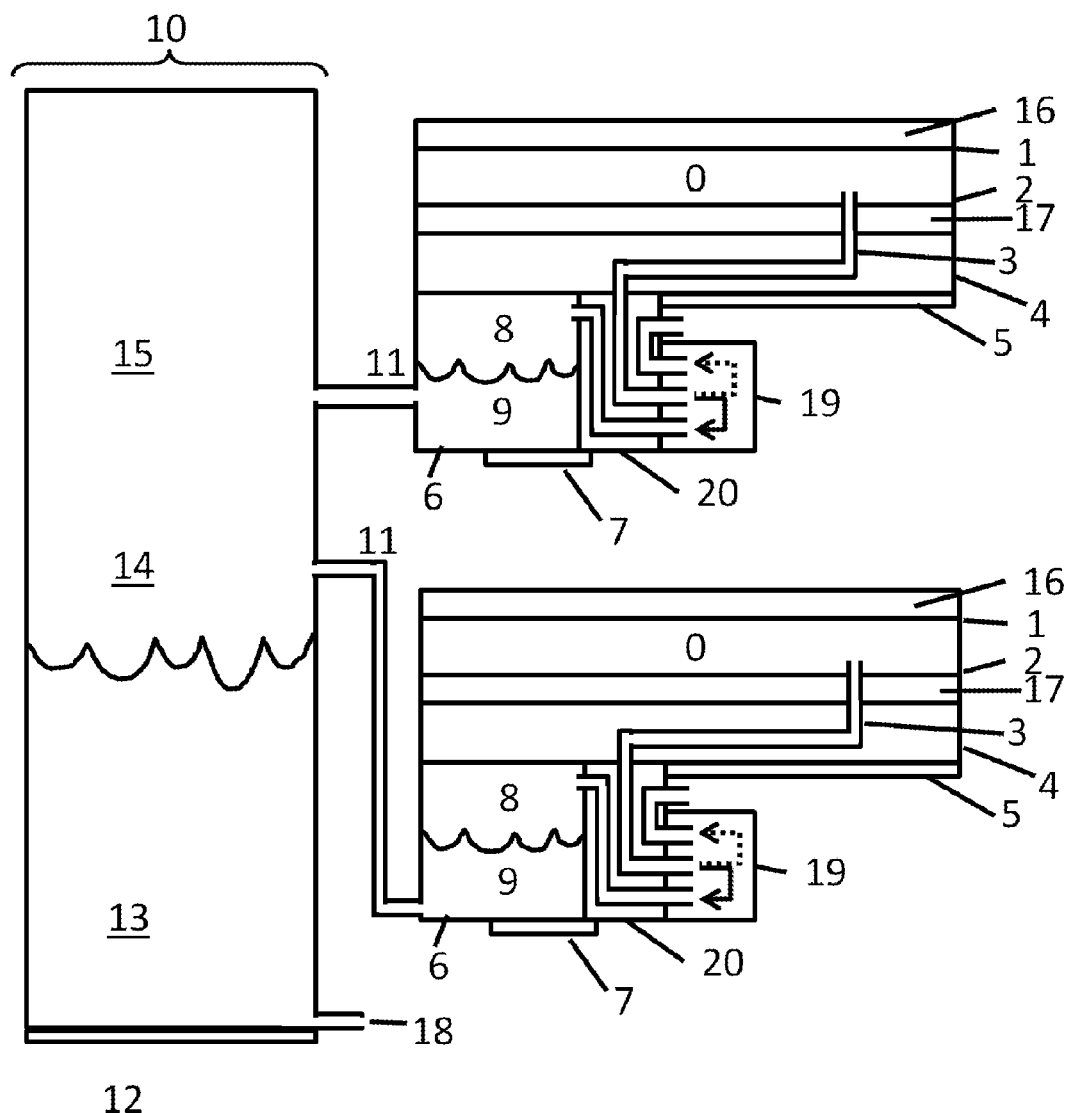
FIG. 5 shows a schematic side view of a humidification system for a plurality of microreactor controllers.

FIG. 5 shows a schematic of a preferred embodiment for implementing a system to reduce evaporation from and condensation in devices containing fluids and gases. While equivalent components and features in FIG. 5 also exist in FIG. 2, FIG. 3A, FIG. 3B, FIG. 4A, FIG. 4B, and FIG. 4C, numbering is changed to differentiate the schematic representations of the components from their model counterparts. The device 0 comprising a top surface 1 and bottom surface 2 is heated by heaters located at the top surface 16 and the bottom surface 17. Humidified gas 8 is delivered to the device through a pressure manifold 4 located under the device through channels 3 in the pressure manifold. The pressure manifold is also heated with a heater 5. Attached to the pressure manifold is a solenoid manifold 20 containing at least one solenoid switch 19 to provide control of gas flow. Attached to the solenoid manifold is the first humidifier 6 comprising humidified gas 8 and a heated first liquid 9. The first humidifier is heated by a heater 7 and is also in contact with the pressure manifold resulting in heating from the pressure manifold heater as well. To replace lost fluid due to evaporation in the humidifier, a channel 11 is connected from the output of a second humidifier 10 to the first humidifier 6. Since only humidified gas 14 is necessary for replacement, the connecting channel 11 is nominally placed in the headspace 15 of the second humidifier to prevent the second humidifier liquid 13 from directly flowing into the first humidifier. The second humidifier is also heated by a heater 12 and comprises a gas input 18 to maintain pressure.

In more detail, FIG. 5 shows a schematic of a humidification system. A first humidified gas 8 is delivered to the device 0 through a heated pressure manifold 4 from a heated first humidifier 6 containing fluid 9. Supplying a first humidified gas to the device minimizes evaporation. Condensation is prevented by setting the temperature of the top surface 1, bottom surface 2, and pressure manifold 4 to values greater than or equal to the temperature required to condense the first humidified gas. Keeping the humidifier on the order of the device size and close to the device enables the introduction of high humidity gas into the device without condensation while relaxing heating requirements. The temperature of all surfaces in contact with the first humidified gas after the first humidifier are equal to or greater than the temperature required to condense the first humidified gas. In a preferred embodiment, the temperatures of the top surface of the device, bottom surface of the device, pressure manifold channel 3, and first humidifier are set to 37 degrees centigrade or between 27 and 40 degrees centigrade, through the use of heaters 5, 7, 16, 17 in direct contact with the objects listed above. In a preferred embodiment, the pressure manifold and first humidifier each contain at least one metal surface to improve temperature uniformity. While the drawing shows the locations of heaters for a preferred embodiment, one with ordinary skill in the art would know that heating can be accomplished with more or less heaters and in many different configurations of heaters. In a preferred embodiment, if switching capability is desired, solenoid switches 19 can be added to the pressure manifold, or an additional manifold 20 located after the first humidifier with added components heated either directly with an additional heater, through the switches themselves, or passively through contact with existing heaters. If the volume of the first humidifier is smaller than required to operate the device, a second humidifier 10 with associated heater 12 of larger volume containing a second humidified gas 14 and fluid 13 can be connected at the input to the first humidifier. In a preferred embodiment, the volume of the first humidifier is less than 10 milliliters or between 4 and 6 milliliters and the volume of the second humidifier is less than 5 liters or between 0.25 and 1 liter where volume refers to the combined fluid and gas volume. In a preferred embodiment, the temperature of the second humidifier is between 20 and 100 degrees centigrade or 37 degrees centigrade. The temperature of the channel 11 between the first and second humidifier need not be higher than the temperature required for the second humidified gas to condense but must be higher than the temperature required for the fluid in the second humidifier to freeze. Fluid condensed between the first and second humidifier will enter the first humidifier and supply fluid for the first humidified gas. In a preferred embodiment, the temperature of the connection is uncontrolled at a room temperature of 20 degrees centigrade or between 10 and 30 degrees centigrade and the connection is a 8 foot long tube or between 2 and 10 foot long tube. In a preferred embodiment, one or more channels are connected between the headspace 15 of the second humidifier and one or more first humidifiers. This connection strategy ensures that condensed fluid and humidified gas are delivered independently to each first humidifier.

Figure 6A:
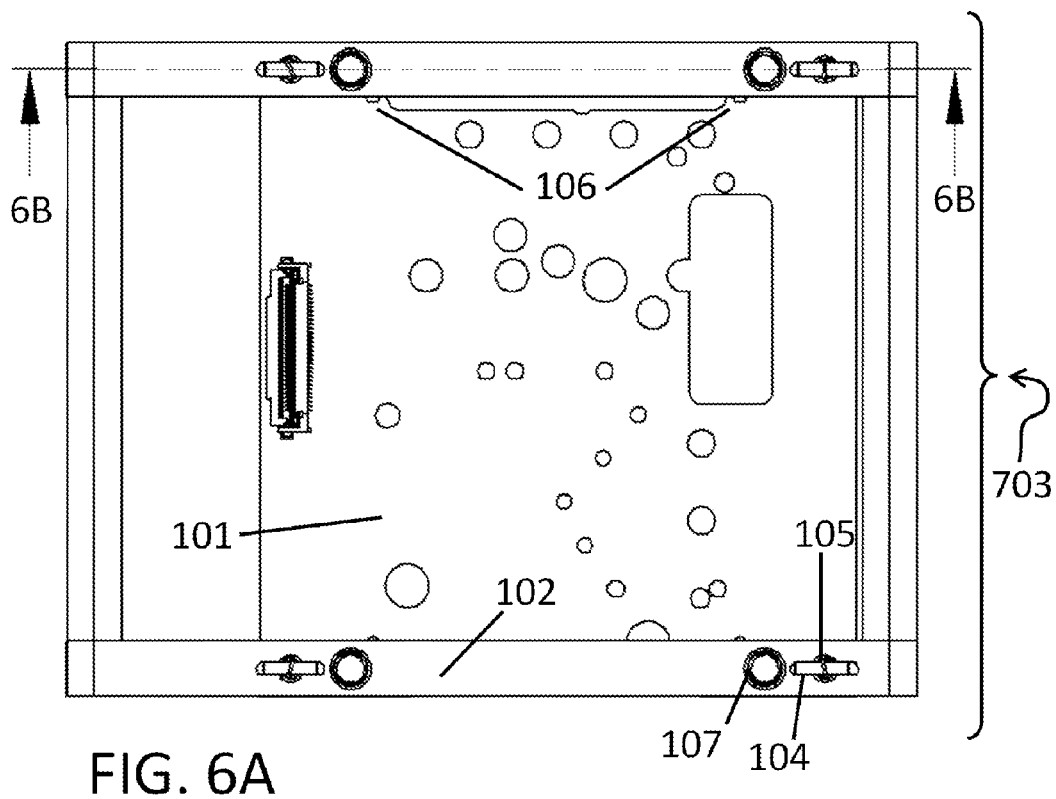
FIG. 6A shows a top view of a heater and a hinged lid.

Referring now to a preferred embodiment in more detail, FIG. 6A shows the lid assembly 703 comprising a top heater 101 and a hinged lid frame 102. The top heater 101 supported on to the hinged lid frame 102 using extension springs 105 fastened by mechanical supports 104 such as a dowel pin. Spring pins 107 push against the top heater 101 such that the extension springs 105 are extended beyond their relaxed length. The heater has alignment holes 106 as part of an aligner to align the top heater with a microreactor device 706.

Figure 6B:
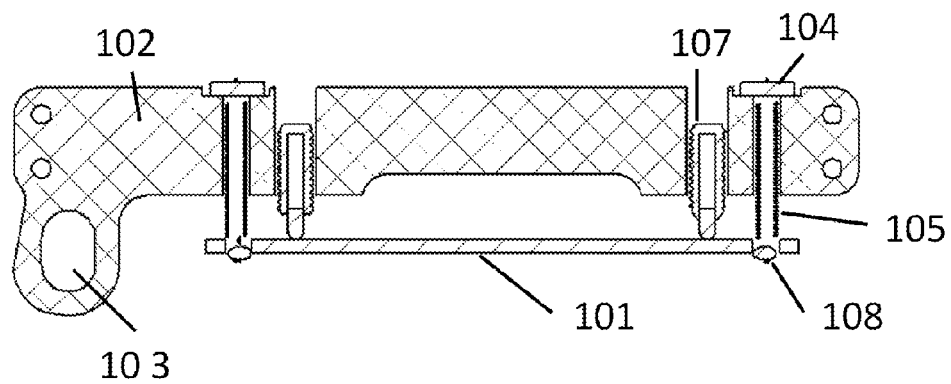
FIG. 6B shows a side view cross-section of a heater and a hinged lid.

Referring now to a preferred embodiment in more detail, FIG. 6B shows a section view of FIG. 6A along the section line 6B-6B. The hinged lid frame 102 comprises hinge pin holes 103 to attach the hinged lid frame 102 to a supporting structure. The heater 101 is attached to hinged lid 102 through extension springs 105. The extension springs 105 are attached to mechanical support 104 on the hinged lid frame 102 and mechanical support 108 on the heater 101. The heater 101 is also pushed away from the hinged lid 102 using spring pins 107 attached to the hinged lid 102.

Now in more detail, FIG. 6A and FIG. 6B show a top heater 101 attached to a hinged lid frame 102 such that the top heater 101 can be moved laterally to be aligned to a supporting structure or microreactor device 706. To ensure contact under pressure between the top heater 101 and the structure or microreactor device 706, spring pins 107, apply pressure when the top heater 101 is pushed against the structure or device, compressing the spring within the spring pin. To secure the top heater 101 to the hinged lid frame 102, extension springs 105 are used and secured with mechanical supports 104, 108. By attaching the top heater 101 to the hinged lid frame 102 using extension springs 105 or any other deformable object, the top heater 101 is able to move with respect to the hinged lid frame 102 which is usually necessary if the top heater 101 is intended to align to a supporting structure, in this case by using alignment holes 106 or other mechanical alignment structure. The alignment holes are useful if the top heater 101 comprises other structures which should be aligned to the supporting structure or device, such as optical, fluid, or pneumatic components. The hinged lid frame 102 is attached to another supporting structure or hinge through holes 103 which allows the hinged lid frame 102 to rotate on the axis of the holes 103. The holes 103 can be circular or oval shaped to accommodate supporting structures underneath the top heater 101 which are of varying sizes and thicknesses.

In further detail, in FIG. 6A and FIG. 6B, the top heater 101 can have a thickness of 0.03125 inch or between 0.02 and 0.125 inch, a length of 3 inch or between 1 inch and 10 inch, and a width of 2.5 inch or between 1 inch and 10 inch. The top heater 101 can be made of rigid materials such as but not limited to fiberglass, epoxy, acrylic, copper, aluminum, or steel. The hinged lid frame 102 can be of similar size to the heater, with a length of 4 inches or between 1 inch and 10 inches, a width of 3 inches or between 1 inch and 10 inches, and a thickness of 0.4 inches or between 0.1 inches and 10 inches. The hinged lid frame 102 can also be made of rigid materials such as but not limited to fiberglass, epoxy, acrylic, copper, aluminum, or steel. Holes 103 on the hinged lid frame 102 can be 0.25 inch diameter, or between 0.0625 and 2 inch diameter if circular. If non-circular, holes 103 can be 0.25 inch wide or between 0.0625 and 2 inch wide and 0.5 inch long or between 0.0625 and 2 inch long. Extension springs 105 can be 0.4 inch long or between 0.04 inch and 2 inch long when unextended and a diameter of 0.09 inch or between 0.04 inch and 0.5 inch and can be made of any spring material such as but not limited to steel, stainless steel, bronze, or brass. Mechanical supports 104, 108 can physically be part of the top heater 101 and hinged lid 102 or be additional structures such as rods or bars made of materials such as but not limited to fiberglass, epoxy, acrylic, copper, aluminum, steel, nylon, teflon, or polycarbonate and can be 0.0625 inch wide or between 0.02 and 1 inch wide and 0.1 inch long or between 0.02 and 1 inch long. Spring pins 107 can be compression springs or spring pins and can be made of materials such as but not limited to steel, stainless steel, bronze, brass, acetal, or nylon, and can be 0.16 inch or between 0.03125 and 1 inch diameter. Alignment holes 106 can be round or polygonal with a, for example, maximum dimension of 0.0625 inches or between 0.02 and 2 inches.

Figure 7A:
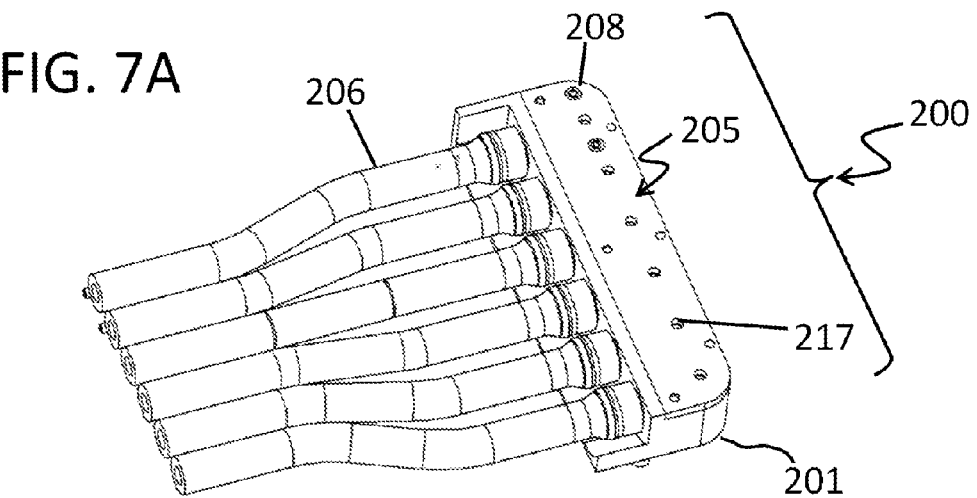
FIG. 7A shows a fluid interface, gasket, and tubing.
Figure 7B:
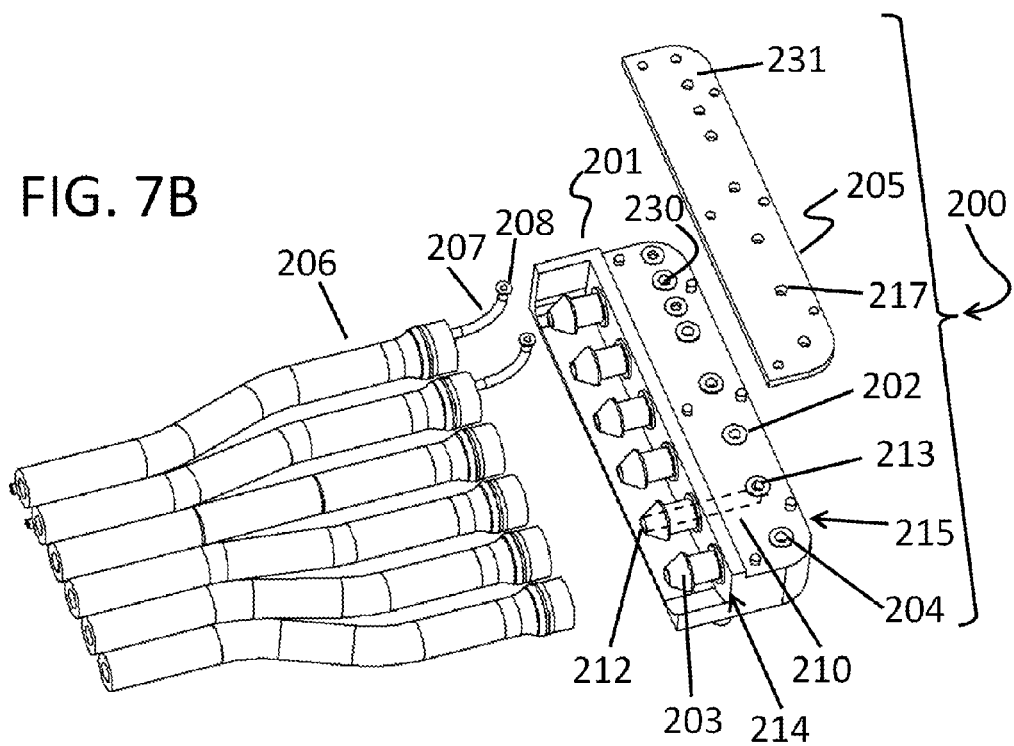
FIG. 7B shows an exploded view of a fluid interface, gasket, and tubing.

Referring now to a preferred embodiment in more detail, FIG. 7A shows an isometric view of an assembled fluid interface 200 comprising a fluid interface body 201, a fluid interface gasket 205, and a conduit 206 in fluid communication with the fluid interface body 201. In more detail, FIG. 7B shows an exploded view of FIG. 7A with a fluid interface body 201 comprising a rigid base with protruding rings 202 on a second side 215 and hose barbs 203 on a first side 214. Openings 204 inside the protruding ring 202 and inside the barb 203 result combine to form an internal conduit 210 connecting the ring 202 to the barb 203. Attached to the top surface of the fluid interface body 201 is a fluid interface gasket 205 comprising holes located at the positions of the protruding rings 202. Under pressure, the gasket 205 is compressed onto the rings 202 on the fluid interface 201 top surface resulting in a leak free seal of the ring 202. In one embodiment, fluid is delivered from a conduit 206 connected to the barb 203 through the opening 204 in the protruding ring and out of the corresponding opening 217 in the gasket 205. In another embodiment, a direct tube 207 can be inserted through the opening 230 in the fluid interface body 201 and the opening 231 in the fluid interface gasket 205 such that fluid is delivered through the direct tube 207 rather than directly contacting a conduit 210 in the fluid interface body 201. In this embodiment, the direct tube 207 exiting from the gasket hole 217 can be flared 208 to aid in sealing the direct tube 207 to an external surface.

In even more detail, FIG. 7B shows an exploded view of a fluid interface body 201 for interfacing with fluid bottles to fluid devices. The fluid interface body 201 comprises hose barbs 203 for connecting tubing 206 to flat surfaces of fluid devices. The side 215 of the fluid interface 201 which interfaces with the fluid device comprises protruding rings 202 such that compression of a fluid interface gasket 205 between the fluid interface 201 and the fluid device forms a leak free seal around the ring 202. Reducing the surface area of contact by using a ring 202, or any small surface area structure slightly larger than the opening 204 allows for more compression of the fluid interface gasket 205. This compression seal places the conduit 210 within the fluid interface body in fluid communication with the microreactor device 706. This creates a path from an external conduit 206 to the microreactor device.

Further detail is provided for FIG. 7B. The fluid interface body 201 can be made of any material that can be sterilized by any one of many conventional sterilization methods such as but not limited to autoclave, gamma irradiation, or ethylene oxide such as but not limited to polycarbonate, polysulfone, radel, polypropylene, aluminum, steel, copper, or brass. The fluid interface body 201 can be between 0.01 and 3 inches or less than 12 inches long, between 0.01 and 3 inches or less than 12 inches wide, and between 0.01 and 3 inches or less than 12 inches thick. Protruding rings 202 can be greater than 0.001 inches or between 0.001 and 0.04 inches high and less than the smaller of the length and width of the fluid interface 201 in diameter. openings 204 in the protruding rings 202 are of smaller diameter than the protruding ring 202. Hose barbs 203 can be between 0.03125 inch and 0.25 inch in diameter with holes 204 of lesser diameter and less than 0.5 inch in height or between 0.03125 inch and 0.25 inch in height. The fluid interface gasket 205 made of an elastic material such as but not limited to silicone, butyl rubber, EPDM, or viton. Fluid interface gaskets 205 can have length and width of thickness between 0.01 and 0.25 inch. The conduit 206 or direct tube 207 inserted into openings 204 or into barbs 203 of the fluid interface body 201 can be made of plastic or rubber such as viton, tygon, PVC, teflon, BPT, or any other material which is suitable for use with liquids and can be sterilized by any of the sterilization methods known to those with ordinary skill in the art. Conduit 206 and direct tube 207 can be of outer diameter between 0.01 inch and 0.5 inch. For direct tube 207 which has a flare 208, the flare 208 can be between 1% to 1000% larger than the outer diameter of the direct tube 207.

Figure 8A:
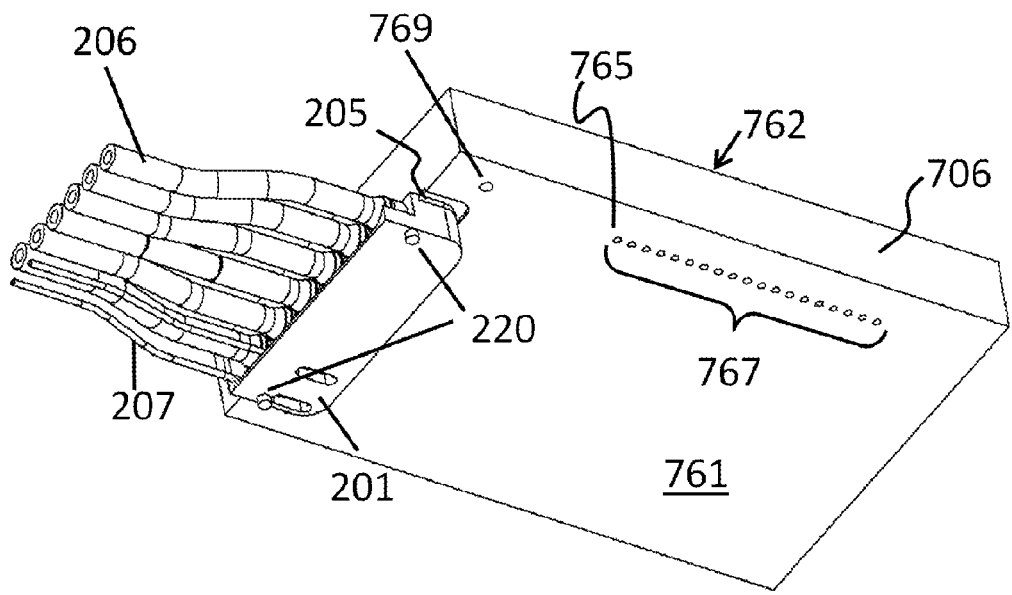
FIG. 8A shows a view of a fluid interface, connected to a microreactor device.
Figure 8B:
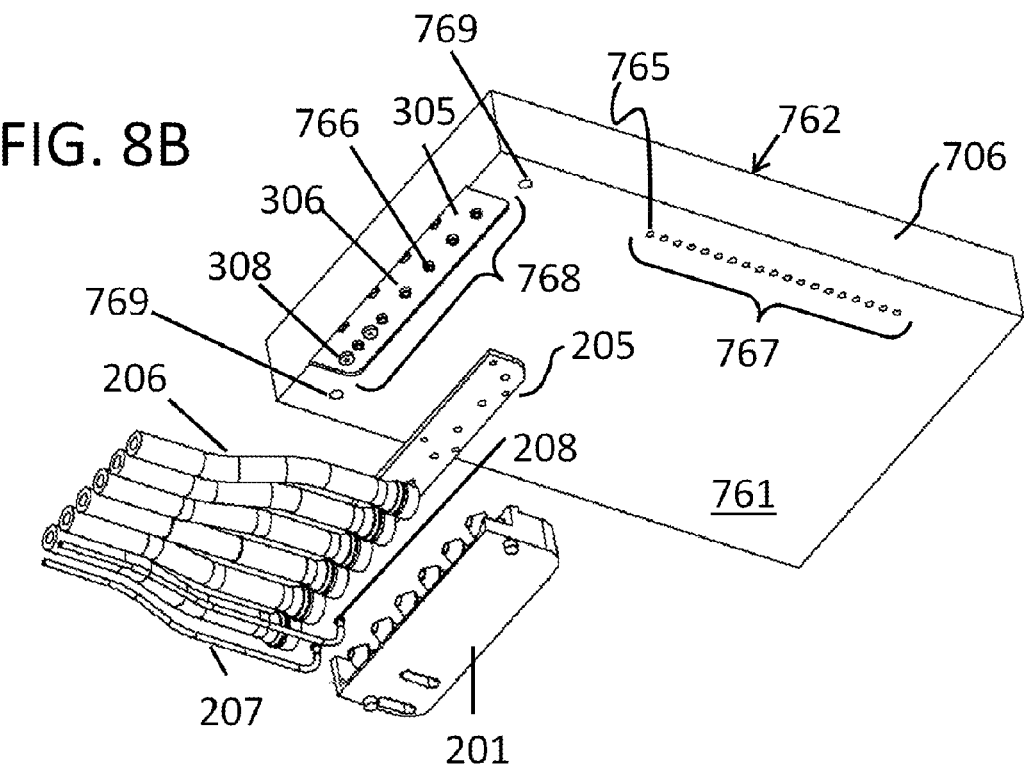
FIG. 8B shows an exploded view of a fluid interface connected to a microreactor device.

FIG. 8A shows an assembled view of a fluid interface body 201, fluid interface gasket 205, and conduits 206 connected to a microreactor device 706. In more detail FIG. 8B shows an exploded view of a fluid interface body 201, fluid interface gasket 205, and conduit 206 connected to a microreactor device 706. The surface 305 of the microreactor device 706 which contacts the fluid interface gasket 205 comprises protruding rings 306 on the microreactor device 706 that have minimal surface area to increase deformation of the fluid interface gasket 205. For connections where fluid is delivered through a direct tube 207, the protruding ring 308 on the microreactor device 706 is of larger surface area than the tube flare 208 such that the tube flare 208 makes contact with the protruding ring 308 of the microreactor device 706. In this configuration, the dimensions are designed such that the fluid interface gasket 205 compresses into the tube flare 208 and seals the tube flare 208 to the protruding ring 308. When aseptic sterile fluid connections are necessary between the fluid interface body 201, fluid interface gasket 205, and microreactor device 706, sections which are sterilized and exposed to air can be protected with peelable adhesive liners using methods such as U.S. Pat. No. 3,865,411 or others known to those with ordinary skill in the art. It should be understood that the protruding rings 306 and 308 encircle openings from the second group 768 of openings in the microreactor device 706.

Referring in more detail to FIG. 8B, the surface 305 of the microreactor device 706 is of similar or larger size than the fluid interface body 201 or fluid interface gasket 205. In a preferred embodiment, the contact surface 305 of the microreactor device 706 has an area of 0.3 square inches or between 0.05 square inches and 5 square inches. The microreactor device 706 can be made of plastic, metal, or any other material which is of higher rigidity than the fluid interface gasket 205 such as but not limited to polycarbonate, acrylic, polysulfone, radel, polypropylene, aluminum, steel, copper, or brass and can be sterilized by any of the sterilization methods known to those with ordinary skill in the art. The protruding rings 306, 308 of the microreactor device 706 can be greater than 0.001 inches or between 0.001 and 0.04 inches high and between 0.02 inch and 0.1 inch in width or less than the smaller of the length and width of the fluid interface body 201 in diameter. The openings from the group 768 surrounded by protruding rings 306, 308 are of smaller diameter than the protruding rings 306, 308.

FIG. 9A shows a top view of the pressure connector and the location of the cross-section 405 for FIG. 9B.

FIG. 9B shows a cross-section view of a pressure connector 401. The pressure connector comprises at least two barbs 402 to interface with tubing and a first conduit 403 and second conduit 406 respectively connecting the openings 407 and 404 and the openings 409 and 408. The pressure connector 401 allows two or more fluid or gas sources entering from the barbs openings 409 and 407 to be connected together when the openings 408 and 404 are in fluid communication through an enclosed external structure.

In more detail, the pressure connector 401 in FIG. 9B can be made of a rigid material such as but not limited to polycarbonate, acrylic, polysulfone, radel, polypropylene, aluminum, steel, copper, or brass. The pressure connector 401 can be 0.375 inch in diameter or between 0.05 and 5 inch in diameter or if the pressure connector 401 is not round but another smooth shape, can be 0.375 inch in its maximum width or between 0.05 and 10 inch in its maximum width. The pressure connector can be 1 inch long or between 0.15 inch and 5 inch long. Hose barbs 402 can be added as external components or can be part of the pressure connector 401. Hose barbs 402 can be 0.1 inch in outer diameter or between 0.02 and 1 inch in outer diameter.

Figure 10A:
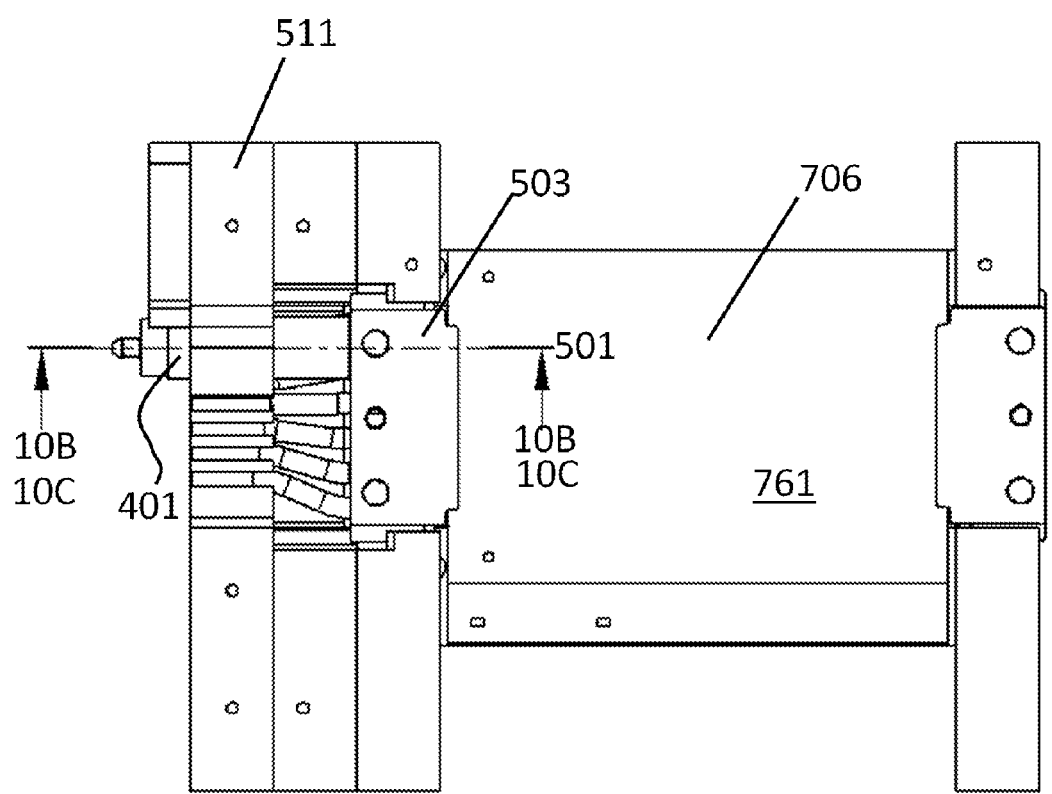
FIG. 10A shows a partial top view of the microreactor controller including a pressure interlock and fluid interface assembly.
Figure 10B:
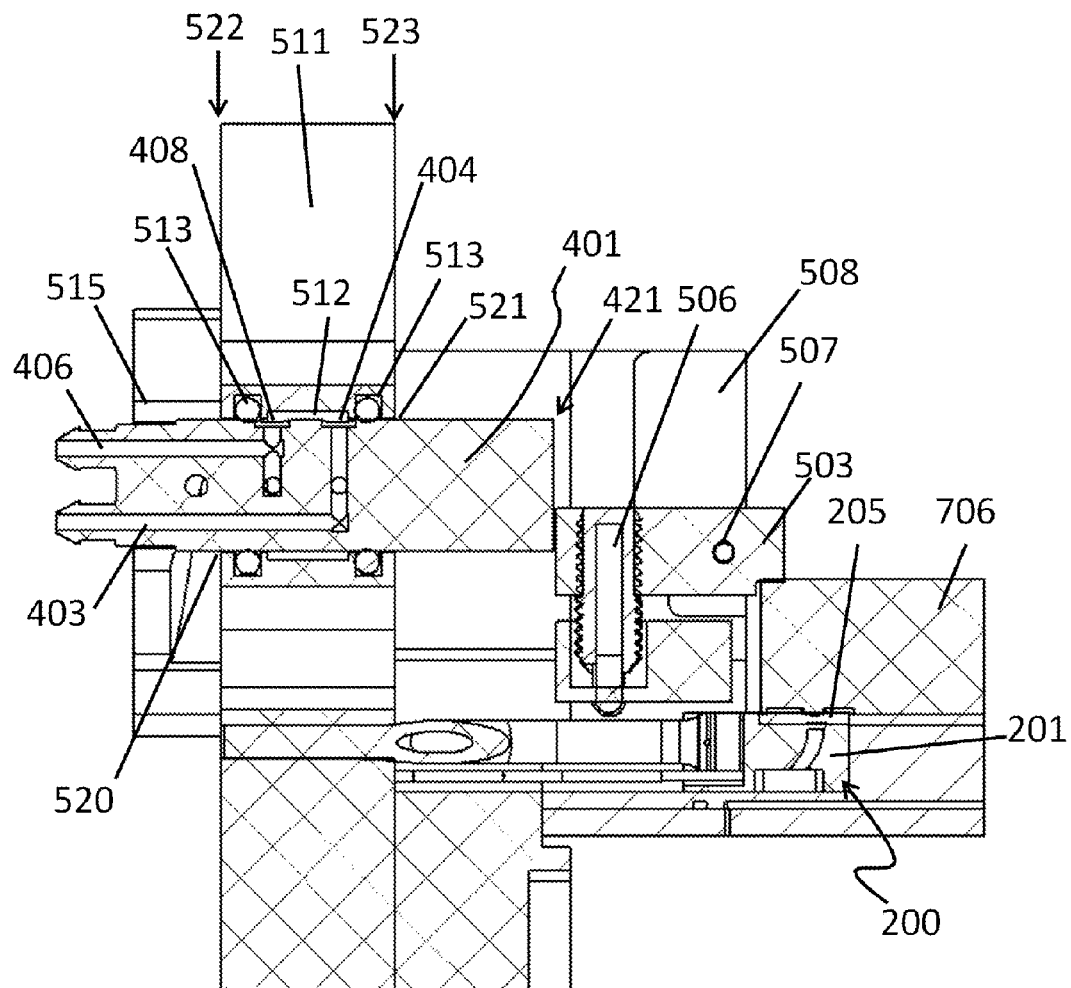
FIG. 10B shows a cross section view of the pressure interlock and fluid interface assembly in a pressurized configuration.

FIG. 10A shows a partial top view of a microreactor controller including a pressure interlock and fluid interface assembly with a section line 501. FIG. 10B shows a cross section view of the pressure interlock and fluid interface assembly in a pressurized configuration along the section line 501 in FIG. 10A.

A clamp 503 applies pressure to the fluid interface 200 and microreactor device 706 and compresses the fluid interface gasket 205 to form a leak free seal. The clamp 503 comprises one or more springs 506 which apply force to the base 504 of the clamp 503 and a pivot point 507 such that the spring force is translated to press the microreactor device against the fluid interface gasket 205. The housing 508 provides the support to the pivot point 507 preventing the upper portion of the clamp 503 from lifting. The clamp housing 508 also supports the clamp base 504 such that the clamp 503 is allowed to move with respect to the microreactor device 706. Other methods of implementing a way to compress the fluid interface gasket 205 between the fluid interface body 201 and microreactor device 706 are also possible, such as but not limited to using springs or screws. Once the clamp 503 is in place, the pressure connector 401 and structural panel 511 can be used to secure the clamp 503 in place. The structural panel 511 comprises a cavity 512 with seals 513 such that a connector 401 of appropriate diameter inserted into the cavity 512 will result in an air tight seal in the volume between the seals 513 of the housing 511. In addition, the structural panel 511 can be attached to the clamp housing 508 to align the pressure connector 401 and the clamp 503. When the pressure connector 401 is pushed towards the clamp 503, and the openings 404 and 408 are between the two seals 513, the first conduit 403 and second conduit 406 in the pressure connector 401 are in fluid communication. In this configuration, the pressure connector 401 can physically stop the clamp 503 from being removed from the device 706. Therefore if the conduits 403 and 406 of the pressure connector 401 are in fluid communication, the device 706 cannot be disconnected from the fluid interface 200. If desired, a locking mechanism 515 can also be used to lock the pressure connector 401 in place when pushed against the clamp 503. This will further prevent the microreactor device 706 from being disconnected from the fluid interface 200 before the conduits 403 and 406 in the pressure connector 401 are disconnected. If this were not the case, a pressure or fluid connection could be active when the microreactor device 706 is disconnected from the fluid interface 201 and fluid or gas could leak into undesired locations.

Figure 10C:
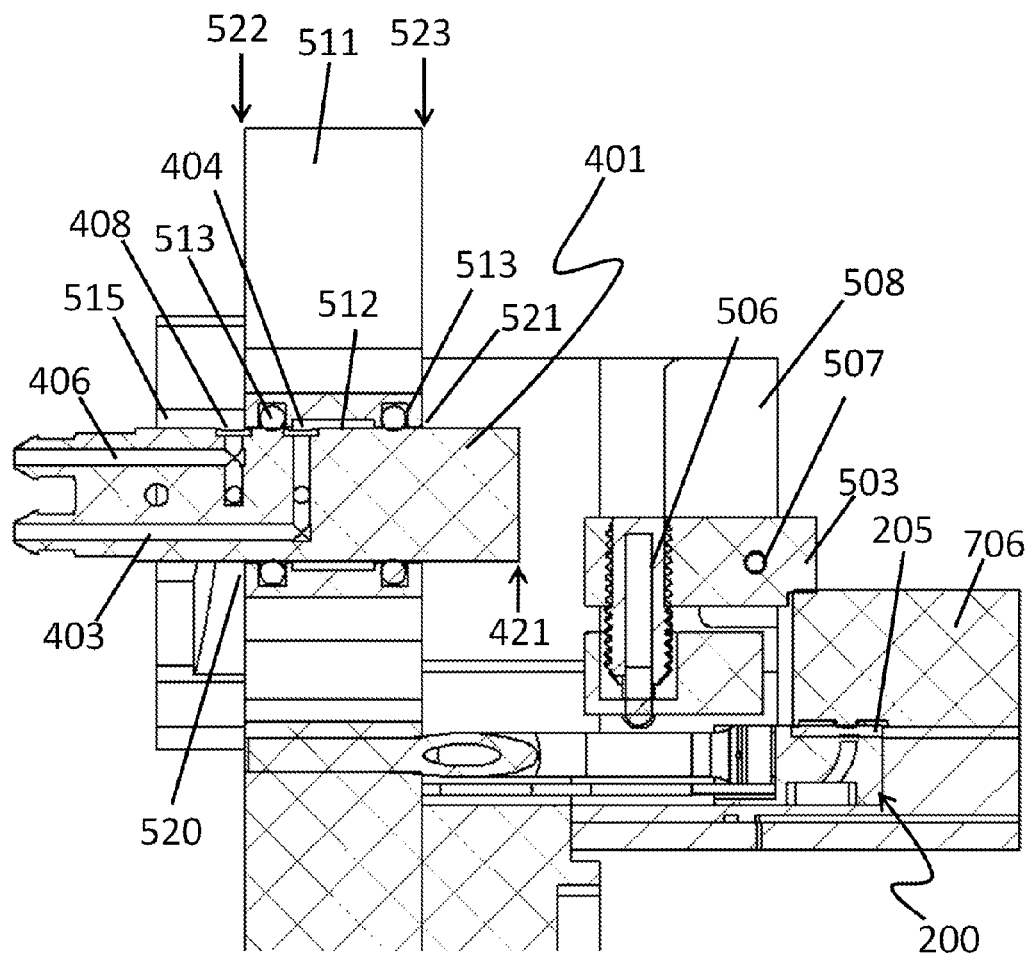
FIG. 10C shows a cross section view of the pressure interlock and fluid interface assembly in a vented configuration.

FIG. 10C and FIG. 10D show the two configurations of the pressure connector 401 in more detail.

The disconnected position depicted in FIG. 10C shows that the opening 404 of conduit 403 is between the seals 513. The opening 408 of conduit 406 is outside of the seals 513 and is open to atmosphere. In this configuration, conduit 403 and 406 are not in fluid communication within the cavity 512 and a pressure in conduit 403 is not transmitted to the conduit 406. In the configuration shown in FIG. 10C with the opening 404 between the seals 513, if a pressure source 912 is in fluid communication with conduit 403, the cavity 512 reaches the same pressure as the pressure source 912 and there is no airflow. If both openings 408 and 404 were outside of the seals 513, for example by pulling the pressure connector 401 further away from the clamp 503, the conduits 406 and 403 would still not be in fluid communication with the cavity 512 and a pressure in conduit 403 would not be transmitted to conduit 406, however the pressure source 912 (shown in FIG. 2B) would then be vented to atmosphere. When the pressure connector is in a position such that at least one of conduits 406 and 403 is vented, therefore depressurizing the fluid sources from the fluid interface 200, there is sufficient space for clamp 503 to be removed and the microreactor device 706 can be removed without excessive fluid leaking from the fluid interface 200.

While the design of the pressure connector 401 comprises two conduits, 403 and 406 which are interconnected when sealed inside the cavity 512 between the seals 513, the pressure connector 401 can contain more or less channels, for example if multiple connections are desired when locked, or if conduits connected to the sealed cavity 512 exist in the structural panel 511 rather than in the pressure connector 401.

Referring in more detail to FIG. 10B, the clamp 503 is a nominally rigid material such as but not limited to polycarbonate, polypropylene, acrylic, aluminum, copper, brass. The outer dimensions of the clamp 503 are similar to those of the fluid interface 201 and can be between 0.01 and 3 inches or less than 12 inches long, between 0.01 and 3 inches or less than 12 inches wide, and between 0.01 and 3 inches or less than 12 inches thick. Springs 506 are capable of supplying between 0.1 and 100 pounds of force and can be compression springs or spring pins made of materials such as but not limited to steel, stainless steel, bronze, brass, acetal, or nylon. The pivot point 507 can be made of a nominally rigid material such as but not limited to acrylic, aluminum, or steel, such that the yield strength of the pivot point 507 is greater than the spring force of the springs or can be part of the clamp 503 material. The pivot point 507 can be a rod or bar 0.0625 inches in width or between 0.02 and 1 inch in width and can extend from the clamp surface by 0.1 inches or between 0.02 and 1 inch. The clamp housing 508 can also be made of a nominally rigid material such as but not limited to polycarbonate, polypropylene, acrylic, aluminum, copper, brass. The housing 508 dimensions are larger than the clamp 503 dimension such that the clamp 503 can restricted by the housing 508. For example the housing 508 can be between 0.1 and 10 inches larger in length, width, and or height of the clamp 503.

In further detail, in a preferred embodiment shown in FIG. 10B, the structural panel 511 is of similar size to the clamp housing 508 to allow the structural panel 511 to attach to the clamp housing 508. While this is the case in a preferred embodiment, similar size is not necessary as the attachment can occur through screws, clamps, bolts, or the like and would only be restricted in size by the mechanism of attachment. The structural panel 511 can be made of any rigid material such as but not limited to polycarbonate, polypropylene, acrylic, peek, Teflon, aluminum, copper, brass, or iron. The seals 513 in the interfacing structural panel can be o-rings or another seal made of an elastomer or rubber material such as but not limited to silicone, butyl rubber, EPDM, or viton and can be between 0.02 and 1 inch in thickness and 0.4 inches or between 0.01 and 4 inches in diameter such that the pressure connector can be sealed by the seals.

Figure 11A:
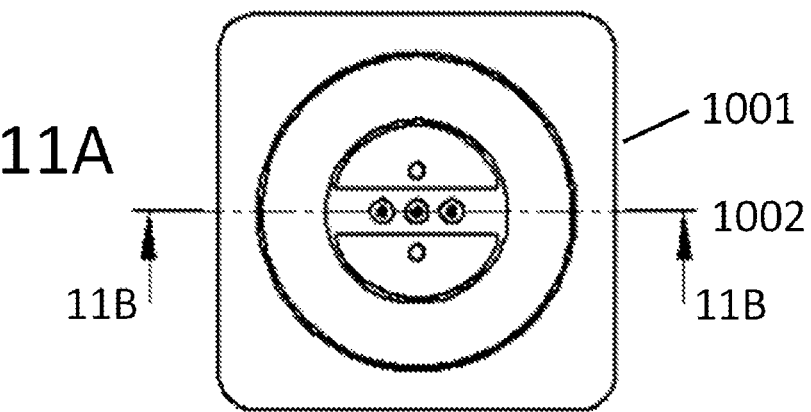
FIG. 11A shows a top view of a fluid bottle with hose barb cap insert.
Figure 11B:
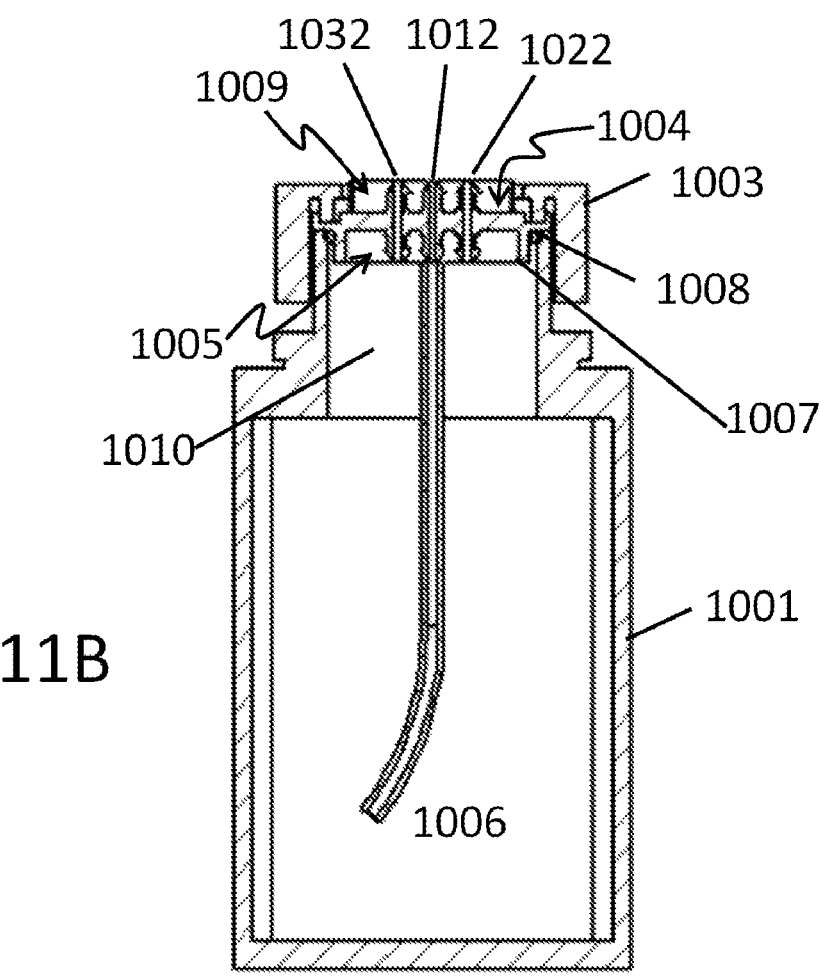
FIG. 11B shows a cross section side view of a fluid bottle with hose barb cap insert.

FIG. 11A shows a top view of a fluid bottle 1001 and a dotted line indicates a section-line 1002. FIG. 11B is a side view cross section of FIG. 11A along the section line 1002 which shows that the bottle cap 1003 comprises an insert 1004 for tubing connections. The insert 1004 comprises inside barbs 1005 and outside barbs 1009 for tubing on both sides such that a tubing connection can be made from outside the fluid bottle 1001 to the bottom of the fluid bottle 1001. While not shown in FIG. 11A, but illustrated schematically in FIG. 2B, a desired tubing connection would be from the external hose barb 1009 to the fluid interface 200 conduit 206. The insert 1004 also comprises a ring 1007 of smaller perimeter than the opening of the fluid bottle and an o-ring 1008 outside of the ring 1007 to enable a seal between the insert 1004 and the fluid bottle 1001. The fluid bottle cap 1003 comprises a hole for the insert 1004 and the insert 1004 is sealed against the fluid bottle 1001 by screwing on the cap 1003. An insert 1004 and bottle 1001 configured in this way allows a fluid bottle 1001 to be sealed with defined inputs and outputs from the bottle 1001.

Referring in more detail to FIG. 11B, the fluid bottle 1001 is a bottle which can be autoclaved, such as a glass or polypropylene bottle, with a cap made of a rigid sterilization stable plastic or metal such as but not limited to polypropylene, polycarbonate, aluminum, or brass. In a preferred embodiment, fluid bottles 1001 can be commercial bottles such as those purchased from companies such as VWR or Nalgene. The insert 1004 is also made of a rigid sterilization stable plastic or metal such as but not limited to polypropylene, polycarbonate, aluminum, or brass. The o-ring 1008 of the insert 1004 is made of an elastomer or rubber material such as but not limited to silicone, butyl rubber, EPDM, or viton. The insert 1004 can be 5% smaller in diameter or between 1% and 50% smaller than the bottle cap 1003. The insert 1004 can contain 3 hose barbs 1005, or between 1 and 64 hose barbs 1005. The hose barbs 1005 can be added as external components or can be part of the insert 1004. Hose barbs 1005 can be 0.1 inch in outer diameter or between 0.02 and 1 inch in outer diameter 1005.

EXAMPLES

Examples of preferred embodiments are described herein.

An example apparatus 601 to operate a microreactor device 706, the microreactor device 706 having a first side 761 and a second side 762, said first side 761 having a first opening 765 among a first group of openings 767 for air pressure, and a second opening 766 among a second group of openings 768 for liquids, the apparatus comprised: a middle heater 801; a heated base plate manifold 800, formed by bonding together base plate top 802 and base plate bottom 803, comprised a thermally conductive material, such as aluminum, that was in thermal communication with the middle heater 801, a conduit 805 with a first opening 810 that was on a first substantially planar surface 812 of the base plate and a second opening 811 that was on a second substantially planar surface of the base plate 813, said second opening was in fluid communication with the first opening 765 of the microreactor device 706; a first pressure source 910; a reservoir, comprised a thermally conductive reservoir layer 901 bonded to another reservoir capping layer 902, the thermally conductive reservoir layer 901 was in thermal communication with the heated base plate manifold 800 and was in fluid communication with the first pressure source 910; a solenoid switch 904 with a first port that was in fluid communication with the first opening 810 of the conduit 805 and a second port that was in fluid communication with the humidifier reservoir 900; and a top heater 101 that was in thermal communication with the second side 762 of the microreactor.

For this example, the microreactor device was operated by switching the pneumatic pressures in a series of openings in the device to, for example, open and close various valves or to actuate mixing structures. It was preferred to use a humidified gas to deliver the pneumatic pressures to minimize evaporation in the microreactor device. This was accomplished by heating the source gas in the presence of liquid water in a reservoir. The flow of humidified gas was controlled by a solenoid switch. To maintain the humidity of the gas and to prevent condensation of the humidified gas, the temperature of the conduit and the temperature of the microreactor device were maintained above the condensation threshold. This was accomplished by delivering the humidified gas to the microreactor device through a conduit in the heated base plate and also by heating the microreactor device on its top and bottom side. Maintaining the top heater temperature higher than the bottom heater temperature ensured condensation free operation. The heated base plate was fabricated by machining channels into an aluminum plate 803 and bonding it to another aluminum plate 802. Holes at the endpoints of the channels 805 that were on the top plate, but could have either on the top plate or the bottom plate, completed the conduits through the base plate. The humidification reservoir was similarly fabricated by bonding an aluminum plate with machined cavities to a flat plate to form an enclosed volume. Various holes provided access to the volume to introduce water for humidification and a source of air pressure. This humidified gas was routed through a manifold to the appropriate ports of solenoid switches which alternately connected each conduit in the top plate with the humidified pressure reservoir, or vented the conduit to atmosphere. It should be clear to those of ordinary skill in the art how this example was constructed or similar apparatus may be constructed using conventional manufacturing techniques such as machining and bonding.

An example for mounting the microreactor device 706 in a way to place the first opening of the microreactor 765 in fluid communication with the second opening 811 of the base plate 800 used an aligner, comprised, for example, two cylindrical posts 830 in the base plate that mated with two holes 769 in the microreactor device to mechanically constrain the position of the microreactor with respect to the base plate so the opening in the microreactor 765 was aligned with the second opening 811 of the base plate; a first gasket 815 that was in contact with the second surface of the base plate 813, said first gasket 815 had an opening 817 coincident with the second opening 811 of the base plate 800; and a clamp 503 that secured the first side of the microreactor device in a fixed position relative to the second substantially planar surface of the base plate 813 such that the first opening 765 on the first side 761 of the microreactor device was in fluid communication with the second opening 811 of the conduit in the base plate through the opening in the first gasket.

Using this example, a large number of openings which corresponded to valves or other pressure driven structures, were aligned to a large number of conduits 805 in the base plate 800. The first gasket 815 conformed to the second substantially planar surface 813 of the base plate and the first surface 761 of the microreactor and formed a seal. The clamp 513, or in general two clamps served to provide a force to hold the microreactor onto the gasket, and maintained the seal. To be precise, the clamps held the microreactor device in a fixed position relative to the substantially planar surface of the base plate which allowed for other components, such as a thin middle heater 801 to be placed between the microreactor 706 and the base plate 800. The term substantially planar is used to allow for surface relief features in the base plate or the microreactor device.

In addition to operating a microreactor device with a pressurized gas under conditions to minimize evaporation from the microreactor device and to minimize condensation in the microreactor device, it was preferred to also exchange liquids with the microreactor device. In particular for certain applications such as conducting bioreactions, it was preferred to exchange liquids with the microreactor device aseptically. To deliver fluids aseptically, all surfaces that contacted the fluid were sterilized. This was accomplished by autoclaving or gamma irradiating, although a variety of other options including dry heat, steam heat, ethylene oxide gas, or other methods to kill potential contaminants could have been used. For preferred embodiments of the invention, the microreactor device was sterilized using gamma irradiation and packaged aseptically. To avoid sterilizing the entire microreactor controller 601 it was preferable to have a removable fluid delivery subsystem that was sterilized separately from the microreactor controller. One embodiment, among many, was a rack of bottles with conduits connected to a fluid interface which were efficiently coupled to the microreactor device. Aseptic coupling was accomplished by covering the liquid openings 768 on the microreactor device and the openings of the fluid interface gasket 217 with sterilizable tape. It should also be noted that to maintain sterility the gasket 205 was bonded to the fluid interface body 201 using an adhesive tape. Also, during autoclave of the fluid interface, mechanical pressure was applied to the tape using a standard binder clip to prevent the tape from debonding during autoclaving. The sterilizable tape was attached to pull tabs that were used to remove the sterilizable tape for the microreactor and the fluid interface simultaneously, in a way known in the art and described in U.S. Pat. No. 3,865,411, when the microreactor device and the fluid interface were held together manually just prior to clamping.

An example embodiment comprised the elements described in previous paragraphs to interface a microreactor to humidified pneumatic signals and further comprised: a fluid interface 200 to exchange a fluid between an external source and the microreactor device, said fluid interface comprised: a body 201 which comprised a conduit 210 with a first opening 212 and a second opening 213 on a surface 215 of the body; a conduit 206 that was in fluid communication with the first opening of the body; and a second gasket 205 that was in contact with the second surface 215 of the body, said second gasket 205 had an opening 217 that coincided with the second opening 213 of the body. A cavity 820 in the base plate 800 allowed mounting the fluid interface, 200 such that the gasket of the fluid interface was approximately parallel to the second substantially planar surface of the base plate so the microreactor device 706 could be sealed to both the first gasket 815 and fluid interface gasket 205. An aligner in the form of two alignment posts 220 on the fluid interface mating with two holes 832 in the base plate cavity 820, mechanically constrained the fluid interface with respect to the base plate. The alignment of the fluid interface with the base plate ensured when the microreactor was aligned to the base plate all openings on the microreactor were aligned with their corresponding openings of the base plate and fluid interface. The clamp 503 closest to the fluid interface was configured in a first position that secured the microreactor device to the gaskets. The clamp 503 also had a second position which allowed the microreactor to be removed from the base plate.

Means to deliver liquids to microreactor devices are known in the art. One example was to use liquid flow from a pressure difference from the source to the destination where a liquid from a reservoir was provided under pressure and the flow of liquid was controlled in the microreactor using valves. One embodiment was to use a container, such as a bottle 1001 with a cap 1003 and insert 1004 that provided an air tight seal but for three openings, one used to fill the bottle with liquid 1032, another used to draw liquid from the bottle 1012, and another used to pressurize 1022 the headspace 1010 of the bottle which provided a driving pressure for the liquid. A conduit 1006 with one end in communication with the opening 1012 and the other end at the bottom of the bottle permitted fluid to leave the bottle through the opening 1012 when the headspace 1010 was pressurized. Typically, the opening 1012 was connected to a conduit 206 with a distal end connected to an opening 212 of the fluid interface.

It was a preferred embodiment to provide a pressure interlock to prevent decoupling of the microreactor from the fluid interface while the bottles were pressurized. Otherwise, if the microreactor were decoupled while the bottles 1001 were still under pressure, liquid would have been forced from the fluid interface and made undesirable contact with other surfaces. In a preferred embodiment, this function was provided by a pressure interlock whereby a mechanical component was configured to connect a pressure source to a bottle headspace and also blocked the removal of a clamp that held the microreactor 706 and fluid interface 200 together.

A preferred embodiment of a pressure interlock comprised: a structural panel 511 with a first fixed position with respect to the first position of the clamp 503; a cavity 512 within the structural panel with a first opening 520 that was on a first side 522 of the structural panel and a second opening 521 that was on a second side 523 of the structural panel 512, said openings had the same cross section and were aligned such that a prism with the same cross section as the opening, but scaled by 0.99 would pass through both openings; a seal 513 that was at the first opening 520 and a seal 513 that was at the second opening 521 allowed that the insertion of a prism with cross section approximately equal to the cross section of the first opening formed an enclosed volume inside the structural panel; a pressure connector 401, that was in the shape of a prism with cross-section approximately the same as the first opening 520 of the cavity, comprised a first conduit 403 with a first opening 404 that was on a radial face of the pressure connector and a second opening 407 that was on a face of the pressure connector, which was preferably at the end of a hose barb 402 that was in fluid communication with a second pressure source 912 and comprised a second conduit 406 with a first opening 408 that was on the radial face of the pressure connector and a second opening 409 that was on a face of the pressure connector, said second opening 409 was in fluid communication with the inlet 1022 of the container; a first axial position (FIG. 10B) of the pressure connector where the first conduit 403 within the pressure connector and second conduit 406 within the pressure connector were in fluid communication within the cavity 412 and where an axial face 421 of the pressure connector constrained the clamp 503 in the first position; a second axial position (FIG. 10C) of the pressure connector where the first conduit within the prism was not in fluid communication, within the cavity, with the second conduit within the prism; and a second pressure source 912 that was in fluid communication with the second opening 407 of the first conduit 403 within the pressure connector 401.

Example methods using the apparatus described in previous examples included a first example method that comprised the steps where: the temperature of the base plate was controlled to a first temperature range T1; the temperature of the top heater was controlled to a second temperature range T2; and the solenoid switch was opened and closed. Condensation within the microreactor devices 706 was minimized by setting the first temperature range T1 lower than the second temperature range T2.

A second example method comprised the steps where: the fluid interface was inserted and aligned into the cavity; the microreactor was aligned to the base plate using an aligner; and the clamp was configured in the first position which sealed the device to the gasket of the fluid interface.

A third example comprised the steps where: a container, conduits in fluid communication with the container, a fluid interface, and a first sterilizable tape covering the openings of the fluid interface were sterilized; the container was filled with sterilized fluid; the fluid interface 200 was inserted and aligned to a cavity in a base plate 820; the sterilized microreactor device with a second sterilizable tape which contacted the first surface of the first sterilizable tape with the first surface of the second sterilizable tape was aligned to the base plate; the first and second sterilizable tape was simultaneously removed; and a clamp was configured in a first position that sealed the microreactor device to a gasket of the fluid interface.

A fourth example comprised the steps where: a container, conduits in fluid communication with the container, a fluid interface, and a first sterilizable tape covering the openings of the fluid interface were sterilized; the container was filled with sterilized fluid; a pressure connector was configured to a second axial position, and then a fluid interface was inserted into the cavity of a base plate and then the structural panel was fixed in its first position and then the microreactor device was aligned to the base plate with an aligner, and then the first surface of the first sterilizable tape was contacted to the first surface of the second sterilizable tape, and then the first and second sterilizable tape were simultaneously removed, and then the clamp was configured in the first position, and then the pressure connector was configured in the first axial position.

Definitions

Microreactor: This term refers to miniature devices with spatial dimensions many times smaller than the analogous macroscopic system. Exemplary microreactor devices may have two spatial dimensions on the order of 100 microns or 10 cm and a third spatial dimension on the order of 1 micron or 1000 microns. A microreactor generally may serve different purposes, such as a microreactor for performing a chemical reaction, or a microreactor for performing a fermentation or cell culture, otherwise known as a microbioreactor. Such microreactors may be housed or supported by a larger physical structure, such as a block of plastic measuring 2 inches by 3 inches by 0.5 inches.

Substantially planar: This term refers to a geometry where a third spatial dimension is less than 10 percent of the other two spatial dimensions. An example would be a 3 inch by 4 inch plate with channels less than 0.3 inches deep, or ridges less that 0.3 inches high.

solenoid switch: This term refers to electro mechanical devices used to switch the flow of a fluid between one or more ports. A port refers to an opening on the surface of a face of the solenoid switch, or a conduit within the solenoid switch. An example is a 3-way solenoid switch with one common port, a normally closed port, and a normally open port. When the solenoid is not energized, the common port is in fluid communication with the normally open port and not in fluid communication with the normally closed port. When the solenoid is energized, the common port is in fluid communication with the normally closed port and not in fluid communication with the normally open port.

aligner: This term refers to a mechanical structure used to align one part with another part. One example is a pair o pins, or protruding cylinders in one part and a pair of holes or circular openings in another part. The diameter of each hole would be chosen such that the hole would fit over the corresponding pin, yet constrain the lateral motion of the parts with respect to each other. An example of a pin-hole pair is a pin with 0.0625 inch diameter and a hole 0.0635 inches. In general an aligner comprises multiple mechanical features such as multiple holes and multiple pins. The position of the holes and pins are chosen such that, for example, when the holes and pins are aligned, the first opening of the microreactor device is aligned to the opening of the first gasket and the second opening of the microreactor device is aligned to the opening of the second gasket and more generally, openings of the microbioreactor are aligned to openings in the heated base plate manifold or fluid interface connector.

fluid: This term refers in general to a liquid or a gas.

manifold: This term refers to an object comprising an internal fluid conduit, preferably an object comprising a plurality of internal fluid conduits, with openings to supply or remove fluid from the conduits.

prism: This term refers to an object with constant cross-section. It can be defined by a two dimensional cross-section determined by a closed curve and a length orthogonal to the cross section. For example, a cylinder with circular cross section.

cross-section of an opening approximately equal to the cross section of a prism: In this relationship the term approximately equal is used to allow for the prism to be slightly smaller than the opening so the prism may to pass through the opening. At the same time, the size and shape of the prism cross-section should be similar enough to the opening to facilitate sealing the opening against the prism with a seal. An example would be a 0.375 inch diameter opening in a 0.50 inch thick plate and a 0.370 inch diameter cylinder. Two seals with inner diameter 0.365, residing in two o-ring grooves on either side of the opening would seal against the cylinder inserted through the opening.

conduit: This term refers in general to enclosed fluid flow paths such as a tube, or pipe, or buried channel suitable for transporting fluid from one location to another.

pressure source: This term refers to a container with a gas maintained in a specified pressure range such as the storage tank of an air compressor, or more generally the storage tank and any conduits connected to said storage tank.

structural panel: This term refers to a solid material used to provide support for components. A structural panel may also have features such as cavities or channels to provide additional functionality. For example, in a preferred embodiment, a structural panel is a one half inch thick piece of polycarbonate, approximately 4 inches by 6 inches in lateral dimensions comprising a cavity and openings to accommodate the prism. In addition, a preferred embodiment of a structural panel has rectangular cutout and grooves to accommodate various conduits.

Thus, specific compositions and methods of a system and methods to operate microreactor devices have been disclosed. It should be apparent, however, to those skilled in the art that many more modifications besides those already described are possible without departing from the inventive concepts herein. The inventive subject matter, therefore, is not to be restricted except in the spirit of the disclosure.

Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Having thus described the invention, what is claimed as new and secured by letters patent is:

1. An apparatus to operate a microreactor device, the microreactor device having a first side and a second side, said first side having a first opening and a second opening, the apparatus comprising:
   a first heater;
   a base plate, in thermal communication with the first heater, comprising: a thermally conductive material; and a control conduit with a first opening on a first substantially planar surface of the base plate and a second opening on a second substantially planar surface of the base plate, said second opening in fluid communication with the first opening of the microreactor device, wherein at least a portion of the length of the control conduit runs laterally across the base plate;
   a first pressure source;
   a reservoir, comprising a thermally conductive material, in thermal communication with the base plate and in fluid communication with the first pressure source;
   a vent conduit;
   a 3-way solenoid switch comprising a first port in fluid communication with the first opening of the control conduit; a second port in fluid communication with the reservoir; and a third port in fluid communication with the vent conduit, wherein the 3-way solenoid switch in an on-state fluidically connects the first port and the second port and fluidically isolates the third port, and the 3-way solenoid switch in an off-state fluidically connects the first port and the third port and fluidically isolates the second port; and
   a second heater in thermal communication with the second side of the microreactor device.

2. The apparatus of claim 1 wherein the first substantially planar surface of the base plate and the second substantially planar surface of the base plate are the same surface.

3. The apparatus of claim 1 further comprising:
   a hinged lid;
   a spring pin protruding from the hinged lid;
   an extension spring;
   wherein the second heater is held against the spring pin by the extension spring; and a top aligner to align the second heater to the microreactor device.

4. The apparatus of claim 3 further comprising:
a light emitting diode;
a waveguide; and
a photodiode.

5. The apparatus of claim 1 further comprising:
a control gasket in contact with the second surface of the base plate, said control gasket having an opening coincident with the second opening of the control conduit in the base plate;
a bottom aligner to align the microreactor device to the base plate; and
a clamp to secure the first side of the microreactor device in a fixed position relative to the second substantially planar surface of the base plate such that the first opening on the first side of the microreactor device is in fluid communication with the second opening of the control conduit in the base plate through the opening in the control gasket.

6. The apparatus of claim 1 further comprising:
a control gasket in contact with the second surface of the base plate, said control gasket having an opening coincident with the second opening of the control conduit in the base plate;
a fluid interface to exchange a fluid between an external source and the microreactor device, said fluid interface comprising: a fluid interface body comprising a feed conduit with a first opening and a second opening on a surface of the body; a source conduit in fluid communication with the first opening of the body; and a fluid interface gasket in contact with the surface of the body, said fluid interface gasket having an opening coinciding with the second opening of the body;
a cavity in the base plate such that when the fluid interface body is mounted in the base plate, the fluid interface gasket of the fluid interface is approximately parallel to the second substantially planar surface of the base plate;
an aligner to align the fluid interface to the base plate;
an aligner to align the microreactor device to the base plate; and
a clamp with a first position that secures the first side of the microreactor device in a fixed position relative to the second substantially planar surface of the base plate, and a second position which allows the removal of the microreactor device from the control gasket and fluid interface gasket.

7. The apparatus of claim 6 further comprising:
a first sterilizable tape with a first surface covering the opening of the fluid interface gasket of the fluid interface; and
a second sterilizable tape with a first surface covering the second opening of the microreactor device.

8. The apparatus of claim 7 further comprising:
a container with an inlet and an outlet; and
a bottle conduit with a first end in fluid communication with the outlet of the container and a second distal end in fluid communication with the inside of the container;
wherein the source conduit of the fluid interface is in fluid communication with the outlet of the container.

9. The apparatus of claim 8 further comprising:
a structural panel with a first fixed position with respect to the first position of the clamp;
a cavity within the structural panel with a first opening on a first side of the structural panel and a second opening on a second side of the structural panel, said openings having the same cross section;
a seal at the first opening and a seal at the second opening such that insertion of a prism with cross section approximately equal to the cross section of the first opening forms a volume inside the structural panel;
a pressure connector in the shape of a prism with cross-section approximately the same as the first opening of the cavity, comprising a first prism conduit with a first opening on a radial face of the pressure connector and a second opening on a face of the pressure connector, and comprising a second prism conduit with a first opening on the radial face of the pressure connector and a second opening on a face of the pressure connector, said second opening of the second prism conduit in fluid communication with the inlet of the container;
a first axial position of the pressure connector where the first prism conduit and second prism conduit are in fluid communication within the structure panel cavity and where an axial face of the pressure connector constrains the clamp in the first position of the clamp;
a second axial position of the pressure connector where the first prism conduit is not in fluid communication within the structure panel cavity with the second prism conduit within the pressure connector; and
a second pressure source in fluid communication with the second opening of the first prism conduit.

10. The apparatus of claim 9 further comprising:
a hinged lid;
a spring pin protruding from the hinged lid;
an extension spring;
the heater held against the spring pin by the extension spring;
an aligner to align the heater to the microreactor device;
a light emitting diode;
a waveguide; and
a photodiode.

11. A method for operating an apparatus to operate a microreactor device, the apparatus comprising:
a first heater;
a base plate, in thermal communication with the first heater, comprising: a thermally conductive material; and a control conduit with a first opening on a first substantially planar surface of the base plate and a second opening on a second substantially planar surface of the base plate, said second opening in fluid communication with the first opening of the microreactor device, wherein at least a portion of the length of the control conduit runs laterally across the base plate;
a first pressure source;
a reservoir, comprising a thermally conductive material, in thermal communication with the base plate and in fluid communication with the first pressure source;
a vent conduit;
a 3-way solenoid switch comprising a first port in fluid communication with the first opening of the control conduit; a second port in fluid communication with the reservoir; and a third port in fluid communication with the vent conduit, wherein the 3-way solenoid switch in an on-state fluidically connects the first port and the second port and fluidically isolates the third port, and the 3-way solenoid switch in an off-state fluidically connects the first port and the third port and fluidically isolates the second port; and
a second heater in thermal communication with the second side of the microreactor device;
the method comprising the steps:
controlling the temperature of the base plate to a first temperature range T1;

controlling the temperature of the second heater to a second temperature range T2; and opening and closing the solenoid switch.

12. The method of claim 11 further comprising the step: controlling the temperature of the reservoir to a third temperature range T3.

13. The method of claim 11 further comprising the step: introducing a fluid into the reservoir.

14. The method of claim 11 where the temperature ranges are constrained such that:

the first temperature range T1 is less than or equal to the second temperature range T2.

15. The method of claim 12 where the temperature ranges are constrained such that:

the first temperature range T1 is less than or equal to the second temperature range T2; and the first temperature range T1 is greater than or equal to the third temperature range T3.

16. The method of claim 11 where the apparatus to operate a microreactor device further comprises:

a control gasket in contact with the second surface of the base plate, said control gasket having an opening coincident with the second opening of the control conduit in the base plate;

a fluid interface to exchange a fluid between an external source and the microreactor device, said fluid interface comprising: a fluid interface body comprising a feed conduit with a first opening and a second opening on a surface of the body; a source conduit in fluid communication with the first opening of the body; and a fluid interface gasket in contact with the surface of the body, said fluid interface gasket having an opening coinciding with the second opening of the body;

a cavity in the base plate such that when the fluid interface body is mounted in the base plate, the fluid interface gasket of the fluid interface is approximately parallel to the second substantially planar surface of the base plate;

an aligner to align the fluid interface to the base plate;

an aligner to align the microreactor device to the base plate; and a clamp with a first position that secures the first side of the microreactor device in a fixed position relative to the second substantially planar surface of the base plate, and a second position which allows the removal of the microreactor device from the control gasket and the fluid interface gasket;

the method further comprising the steps:

inserting the fluid interface into the cavity of the base plate;

aligning the first opening of the microreactor device to the opening of the control gasket and aligning the second opening of the microreactor device to the opening of the fluid interface gasket; and configuring the clamp in the first position.

17. The method of claim 16 where the apparatus to operate a microreactor further comprises:

a first sterilizable tape with a first surface covering the opening of the fluid interface gasket of the fluid interface; and a second sterilizable tape with a first surface covering the second opening of the microreactor device;

a container with an inlet and an outlet; and a bottle conduit with a first end in fluid communication with the outlet of the container and a second distal end in fluid communication with the inside of the container;

wherein the source conduit of the fluid interface is in fluid communication with the outlet of the container;

the method further comprising the steps:

sterilizing the container, the conduits in fluid communication with the container, the fluid interface, and the first sterilizable tape;

filling the container with sterilized fluid;

inserting the fluid interface into the cavity of the base plate;

aligning the first opening of the microreactor device to the opening of the control gasket and aligning the second opening of the microreactor device to the opening of the fluid interface gasket;

contacting the first surface of the first sterilizable tape with the first surface of the second sterilizable tape;

simultaneously removing the first and second sterilizable tape; and configuring the clamp in the first position of the clamp.

18. The method of claim 17, the apparatus to operate a microreactor device further comprising:

a structural panel with a first fixed position with respect to the first position of the clamp;

a cavity within the structural panel with a first opening on a first side of the structural panel and a second opening on a second side of the structural panel, said openings having the same cross section;

a seal at the first opening and a seal at the second opening such that insertion of a prism with cross section approximately equal to the cross section of the first opening forms a volume inside the structural panel;

a pressure connector in the shape of a prism with cross-section approximately the same as the first opening of the cavity, comprising a first prism conduit with a first opening on a radial face of the pressure connector and a second opening on a face of the pressure connector, and comprising a second prism conduit with a first opening on the radial face of the pressure connector and a second opening on a face of the pressure connector, said second opening of the second prism conduit in fluid communication with the inlet of the container;

a first axial position of the pressure connector where the first prism conduit and second prism conduit are in fluid communication within the structure panel cavity and where an axial face of the pressure connector constrains the clamp in the first position of the clamp;

a second axial position of the pressure connector where the first prism conduit is not in fluid communication within the structure panel cavity with the second prism conduit; and a second pressure source in fluid communication with the second opening of the first prism conduit; the method further comprising the steps in the order specified:

sterilizing the container, the conduits in fluid communication with the container, the fluid interface, and the first sterilizable tape;

filling the container with sterilized fluid;

configuring the prism to the second axial position, and then inserting the fluid interface into the cavity of the base plate and fixing the structural panel in its first position;

aligning the microreactor device to the heated base plate manifold and fluid interface using an aligner;

contacting the first surface of the first sterilizable tape with the first surface of the second sterilizable tape and then;

simultaneously removing the first and second sterilizable tape;

configuring the clamp in the first position; and configuring the prism in the first axial position.

* * * * *